US008048848B2

(12) United States Patent
Fares et al.

(10) Patent No.: US 8,048,848 B2
(45) Date of Patent: *Nov. 1, 2011

(54) LONG-ACTING INTERFERONS AND DERIVATIVES THEREOF AND METHODS THEREOF

(75) Inventors: Fuad Fares, Hourfish village (IL); Udi Eyal Fima, Beer-Sheva (IL)

(73) Assignee: Prolor Biotech Ltd., Nes Ziona (IL)

( * ) Notice: Subject to any disclaimer, the term of this patent is extended or adjusted under 35 U.S.C. 154(b) by 221 days.

This patent is subject to a terminal disclaimer.

(21) Appl. No.: 12/216,989

(22) Filed: Jul. 14, 2008

(65) Prior Publication Data

US 2009/0087411 A1    Apr. 2, 2009

Related U.S. Application Data

(63) Continuation-in-part of application No. 11/700,911, filed on Feb. 1, 2007, now Pat. No. 7,553,941.

(60) Provisional application No. 60/764,761, filed on Feb. 3, 2006.

(51) Int. Cl.
| | |
|---|---|
| *A61K 38/21* | (2006.01) |
| *A61K 38/24* | (2006.01) |
| *C07K 1/00* | (2006.01) |
| *C07K 14/56* | (2006.01) |
| *C07K 14/565* | (2006.01) |
| *C07K 14/57* | (2006.01) |
| *C07K 14/555* | (2006.01) |

(52) U.S. Cl. ........... 514/1.1; 514/9.9; 530/351; 530/402
(58) Field of Classification Search .................. None
See application file for complete search history.

(56) References Cited

U.S. PATENT DOCUMENTS

| | | | |
|---|---|---|---|
| 5,177,193 | A | 1/1993 | Boime |
| 5,759,818 | A | 6/1998 | Boime et al. |
| 5,792,460 | A | 8/1998 | Boime |
| 6,238,890 | B1 | 5/2001 | Boime et al. |
| 6,514,729 | B1 * | 2/2003 | Bentzien ............... 435/69.51 |
| 7,094,566 | B2 | 8/2006 | Medlock et al. |
| 7,141,547 | B2 | 11/2006 | Rosen et al. |
| 7,371,373 | B2 | 5/2008 | Shirley et al. |
| 7,553,940 | B2 | 6/2009 | Fares et al. |
| 7,553,941 | B2 | 6/2009 | Fares et al. |
| 2003/0216313 | A1 | 11/2003 | Lustbader et al. |
| 2007/0184530 | A1 | 8/2007 | Fares et al. |

FOREIGN PATENT DOCUMENTS

WO     WO 2005/080544     9/2005

OTHER PUBLICATIONS

Weiss et al. Noncompliance in Neurologic Patients. Current Treatment Options in Neurology 7:419-425 (2005).*
Furuhashi, M. et al; 'Fusing the Carboxy-terminal Peptide of the Chorionic Gonadotropin (CG) β-Subunit to the Common a-Subunit: Retention of O-linked Glycosylation and Enhanced in vivo Bioactivity of Chimeric Human CG', Molecular Endocrinology, 1995, vol. 9, No. 1, pp. 54-63.
Furuhashi, M. et al, 'Processing of O-linked Glycosylation in the Chimera Consisting of a-Subunit and Carboxyl-terminal Peptide of the Human Chorionic Gonadotropin β-Subunit is affected by Dimer Formation with Follicle-stimulating Hormone β-Subunit', Endocrine Journal 2004, vol. 51, No. 1, pp. 53-59.
Schein, Catherine H. The shape of the messenger: using protein structure information to design novel cytokine-based therapeutics. Abstract; Current Pharmaceutical Design, vol. 8/No. 24, pp. 2113-2129 (2002).
Amirizahdeh et al. "Transient and stable expression of biologically active recombinant B-domain-deleted human factor VIII in mammalian cells" Journal of Sciences Islamic Republic of Iran; 16(2):103-112. Spring, 2005.
Boissel et al. "Erythropoietin structure-function relationships. Mutant proteins that test a model of tertiary structure" The Journal of Biological Chemistry,268, 15983-15993, Jul. 25, 1993.
Houdebine et al. "The methods to generate transgenic animals and to control transgene expression" Journal of Biotechnology vol. 98, Issues 2-3, pp. 145-160, Sep. 25, 2002.
Ngo et al. "Computational Complexity, Protein Structure Prediction, and the Levinthal Paradox" The protein folding problem and tertiary structure prediction. pp. 433-440 and 492-495. (1994).
Phillips et al. "The challenge of gene therapy and DNA delivery" Journal of Pharmacy and Pharmacology vol. 53, Issue 9, pp. 1169-1174, Sep. 2001, Abstract Only.
Unalp et al. "Factor VII deficiency associated with Valproate treatment" Pediatrics International vol. 50, Issue 3, pp. 403-405, Jun. 2008.
Wells. "Additivity of mutational effects in proteins" Biochemistry, 29 (37), pp. 8509-8517. (1990).
Weiss et al. "Noncompliance in neurologic patients" Curr Treat Options Neurol. Sep. 2005;7(5):419-23.

* cited by examiner

*Primary Examiner* — Elizabeth C Kemmerer
*Assistant Examiner* — Regina M Deberry
(74) *Attorney, Agent, or Firm* — Pearl Cohen Zedek Latzer, LLP; Mark S. Cohen

(57) ABSTRACT

A polypeptide and polynucleotides encoding same comprising carboxy-terminal peptides (CTP) of chorionic gonadotrophin attached to an IFN protein are disclosed. Pharmaceutical compositions comprising the polypeptide and polynucleotides of the invention and methods of using same are also disclosed.

34 Claims, 9 Drawing Sheets

Underline: Signal sequence
Black letters: Mature protein
Italic: CTP unit

Human Interferon-β 1a-MOD-9010 hIFNβ 1a

AA sequence (Accession No. NP_002167.1)

```
    M   T   N   K   C   L   L   Q   I   A   L   L   L   C   F   S   T   T   A   L   S   M   S
Y   N   L   L   G   F   L   Q   R   S   S   N   F   Q   C   Q   K   L   L   W   Q   L   N   G
R   L   E   Y   C   L   K   D   R   M   N   F   D   I   P   E   E   I   K   Q   L   Q   Q
F   Q   K   E   D   A   A   L   T   I   Y   E   M   L   Q   N   I   F   A   I   F   R   Q
D   S   S   S   T   G   W   N   E   T   I   V   E   N   L   L   A   N   V   Y   H   Q   I
N   H   L   K   T   V   L   E   E   K   L   E   K   E   D   F   T   R   G   K   L   M   S
S   L   H   L   K   R   Y   Y   G   R   I   L   H   Y   L   K   A   K   E   Y   S   H   C
A   W   T   I   V   R   V   E   I   L   R   N   F   Y   F   I   N   R   L   T   G   Y   L
R   N
```

Total: 186 aa

Nucleotides Sequence (Accession No. NM_002176)

```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa accgtgctgg aagagaagct ggaaaaggag gacttcacca ggggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccggct acctgaggaa ctgatgagtc cgcggccgc
```

Underline: Signal sequence
Black letters: Mature protein
Italic: CTP

FIGURE 3A

Human Interferon-β 1a-MOD-9011

IFNβ 1A-CTP DNA and protein sequence

AA sequence (Accession No. NP_002167.1)

| M | T | N | K | C | L | L | Q | I | A | L | L | L | C | F | S | T | T | A | L |
|---|---|---|---|---|---|---|---|---|---|---|---|---|---|---|---|---|---|---|---|
| S | M | S | Y | N | L | L | G | F | L | Q | R | S | S | N | F | Q | C | Q | K |
| L | L | W | Q | L | N | G | R | L | E | Y | C | L | K | D | R | M | N | F | D |
| I | P | E | E | I | K | Q | L | Q | Q | F | Q | K | E | D | A | A | L | T | I |
| Y | E | M | L | Q | N | I | F | A | I | F | R | Q | D | S | S | S | T | G | W |
| N | E | T | I | V | E | N | L | L | A | N | V | Y | H | Q | I | N | H | L | K |
| T | V | L | E | E | K | L | E | K | E | D | F | T | R | G | K | L | M | S | S |
| L | H | L | K | R | Y | Y | G | R | I | L | H | Y | L | K | A | K | E | Y | S |
| H | C | A | W | T | I | V | R | V | E | I | L | R | N | F | Y | F | I | N | R |
| L | T | G | Y | L | R | N | *S* | *S* | *S* | *S* | *K* | *A* | *P* | *P* | *P* | *S* | *L* | *P* | *S* |
| *P* | *S* | *R* | *L* | *P* | *G* | *P* | *S* | *D* | *T* | *P* | *I* | *L* | *P* | *Q* | | | | | |

Nucleotides Sequence (Accession No. NM_002176)

```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa accgtgctgg aagagaagct ggaaaaggag gacttcacca ggggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccggct acctgaggaa cagctccagc agcaaggccc ctccaccttc
601 cctgcccagt ccaagccgac tccctgggcc ctccgataca ccaattctgc cacagtgatg
661 a
```

FIGURE 3B

Human Interferon-β 1a-MOD-9012

IFNβ 1A-CTP-CTP DNA and protein sequence

AA sequence (Accession No. NP_002167.1)

| M | T | N | K | C | L | L | Q | I | A | L | L | L | C | F | S | T | T | A | L |
|---|---|---|---|---|---|---|---|---|---|---|---|---|---|---|---|---|---|---|---|
| S | M | S | Y | N | L | L | G | F | L | Q | R | S | S | N | F | Q | C | Q | K |
| L | L | W | Q | L | N | G | R | L | E | Y | C | L | K | D | R | M | N | F | D |
| I | P | E | E | I | K | Q | L | Q | Q | F | Q | K | E | D | A | A | L | T | I |
| Y | E | M | L | Q | N | I | F | A | I | F | R | Q | D | S | S | S | T | G | W |
| N | E | T | I | V | E | N | L | L | A | N | V | Y | H | Q | I | N | H | L | K |
| T | V | L | E | E | K | L | E | K | E | D | F | T | R | G | K | L | M | S | S |
| L | H | L | K | R | Y | Y | G | R | I | L | H | Y | L | K | A | K | E | Y | S |
| H | C | A | W | T | I | V | R | V | E | I | L | R | N | F | Y | F | I | N | R |
| L | T | G | Y | L | R | N | *S* | *S* | *S* | *S* | *K* | *A* | *P* | *P* | *P* | *S* | *L* | *P* | *S* |
| *P* | *S* | *R* | *L* | *P* | *G* | *P* | *S* | *D* | *T* | *P* | *I* | *L* | *P* | *Q* | *S* | *S* | *S* | *S* | *K* |
| *A* | *P* | *P* | *P* | *S* | *L* | *P* | *S* | *P* | *S* | *R* | *L* | *P* | *G* | *P* | *S* | *D* | *T* | *P* | *I* |
| *L* | *P* | *Q* | | | | | | | | | | | | | | | | | |

Nucleotides Sequence (Accession No. NM_002176)

```
  1 tctagaggac atgaccaaca agtgcctgct gcagatcgcc ctgctgctgt gcttcagcac
 61 caccgccctg agcatgagct acaacctgct gggcttcctg cagaggtcca gcaacttcca
121 gtgccagaag ctgctgtggc agctgaacgg caggctggaa tactgcctga aggacaggat
181 gaacttcgac atcccagagg aaatcaagca gctgcagcag ttccagaagg aggacgccgc
241 cctgaccatc tacgagatgc tgcagaacat cttcgccatc ttcaggcagg acagcagcag
301 caccggctgg aacgagacca tcgtggagaa cctgctggcc aacgtgtacc accagatcaa
361 ccacctgaaa accgtgctgg aagagaagct ggaaaaggag gacttcacca ggggcaagct
421 gatgagcagc ctgcacctga gaggtacta cggcagaatc ctgcactacc tgaaggccaa
481 ggagtacagc cactgcgcct ggaccatcgt gagggtggag atcctgagga acttctactt
541 catcaacagg ctgaccggct acctgaggaa cagctccagc agcaaggccc ctccaccttc
601 cctgccagt ccaagccgac tccctgggcc ctccgacaca ccaatcctgc cacagagcag
661 ctcctctaag gcccctcctc catccctgcc atccccctcc cggctgcctg gcccctctga
721 caccctatc ctgcctcagt gatgaaggtc tggatccgcg ccgc
```

FIGURE 3C

Human Interferon-β 1a-MOD-9013

CTP-IFNβ 1A-CTP-CTP DNA and protein sequence

AA sequence (Accession No. NP_002167.1)

| M | T | N | K | C | L | L | Q | I | A | L | L | L | C | F | S | T | T | A | L |
|---|---|---|---|---|---|---|---|---|---|---|---|---|---|---|---|---|---|---|---|
| S | *S* | *S* | *S* | *S* | *K* | *A* | *P* | *P* | *P* | *S* | *L* | *P* | *S* | *P* | *S* | *R* | *L* | *P* | *G* |
| *P* | *S* | *D* | *T* | *P* | *I* | *L* | *P* | *Q* | M | S | Y | N | L | L | G | F | L | Q | R |
| S | S | N | F | Q | C | Q | K | L | L | W | Q | L | N | G | R | L | E | Y | C |
| L | K | D | R | M | N | F | D | I | P | E | E | I | K | Q | L | Q | Q | F | Q |
| K | E | D | A | A | L | T | I | Y | E | M | L | Q | N | I | F | A | I | F | R |
| Q | D | S | S | S | T | G | W | N | E | T | I | V | E | N | L | L | A | N | V |
| Y | H | Q | I | N | H | L | K | T | V | L | E | E | K | L | E | K | E | D | F |
| T | R | G | K | L | M | S | S | L | H | L | K | R | Y | Y | G | R | I | L | H |
| Y | L | K | A | K | E | Y | S | H | C | A | W | T | I | V | R | V | E | I | L |
| R | N | F | Y | F | I | N | R | L | T | G | Y | L | R | N | *S* | *S* | *S* | *S* | *K* |
| *A* | *P* | *P* | *P* | *S* | *L* | *P* | *S* | *P* | *S* | *R* | *L* | *P* | *G* | *P* | *S* | *D* | *T* | *P* | *I* |
| *L* | *P* | *Q* | *S* | *S* | *S* | *S* | *K* | *A* | *P* | *P* | *P* | *S* | *L* | *P* | *S* | *P* | *S* | *R* | *L* |
| *P* | *G* | *P* | *S* | *D* | *T* | *P* | *I* | *L* | *P* | *Q* | | | | | | | | | |

Nucleotides Sequence (Accession No. NM_002176)

```
  1 tctagaggac atgaccaaca agtgcctgct gcagatcgcc ctgctgctgt gcttcagcac
 61 caccgccctg agcagcagca gctccaaggc cccaccccc  agcctgccca gcccagcag
121 actgccaggc cccagcgaca ccccatcct  gccccagatg agctacaacc tgctgggctt
181 cctgcagagg tccagcaact tccagtgcca gaagctgctg tggcagctga acggcaggct
241 ggaatactgc ctgaaggaca ggatgaactt cgacatccca gaggaaatca agcagctgca
301 gcagttccag aaggaggacg ccgccctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaaccgtg ctggaagaga gctggaaaa
481 ggaggacttc accaggggca agctgatgag cagcctgcac ctgaagaggt actacggcag
541 aatcctgcac tacctgaagg ccaaggagta cagccactgc gcctggacca tcgtgagggt
601 ggagatcctg aggaacttct acttcatcaa caggctgacc ggctacctga ggaacagctc
661 cagcagcaag gcccctccac cttccctgcc cagtccaagc cgactccctg gcccctccga
721 cacaccaatc ctgccacaga gcagctcctc taaggcccct cctccatccc tgccatcccc
781 ctcccggctg cctggcccct ctgacacccc tatcctgcct cagtgatgaa ggtctggatc
841 cgcggccgc
```

FIGURE 3D

Human Interferon-β 1a-MOD-9014

CTP-IFNB-CTP-IFNB DNA and protein sequence

AA sequence (Accession No. NP_000790.2)

```
M T N K C L L Q I A L L L C F S T T A L S
S S S S K A P P P S L P S P S R L P G P S
D T P I L P Q M S Y N L L G F L Q R S S N
F Q C Q K L L W Q L N G R L E Y C L K D R
M N F D I P E E I K Q L Q Q F Q K E D A A
L T I Y E M L Q N I F A I F R Q D S S S T
G W N E T I V E N L L A N V Y H Q I N H L
K T V L E E K L E K E D F T R G K L M S S
L H L K R Y Y G R I L H Y L K A K E Y S H
C A W T I V R V E I L R N F Y F I N R L T
G Y L R N S S S S K A P P P S L P S P S R
L P G P S D T P I L P Q M S Y N L L G F L
Q R S S N F Q C Q K L L W Q L N G R L E Y
C L K D R M N F D I P E E I K Q L Q Q F Q
K E D A A L T I Y E M L Q N I F A I F R Q
D S S S T G W N E T I V E N L L A N V Y H
Q I N H L K T V L E E K L E K E D F T R G
K L M S S L H L K R Y Y G R I L H Y L K A
K E Y S H C A W T I V R V E I L R N F Y F
I N R L T G Y L R N
```

Nucleotides Sequence (Accession No. NM_002176)

```
   1 tctagaggac atgaccaaca agtgcctgct gcagatcgcc ctgctgctgt gcttcagcac
  61 caccgccctg agcagcagca gctccaaggc cccacccccc agcctgccca gccccagcag
 121 gctgccaggc cccagcgaca cccccatcct gccccagatg agctacaacc tgctgggctt
 181 cctgcagagg tccagcaact tccagtgcca gaaactgctg tggcagctga acggcaggct
 241 ggaatactgc ctgaaggacc ggatgaactt cgacatcccc gaagagatca agcagctgca
 301 gcagttccag aaagaggacg ccgccctgac catctacgag atgctgcaga acatcttcgc
 361 catcttcagg caggacagca gcagcaccgg ctggaacgag accatcgtgg agaacctgct
 421 ggccaacgtg taccaccaga tcaaccacct gaaaaccgtg ctggaagaga agctggaaaa
 481 agaggacttc accaggggca agctgatgag cagcctgcac ctgaagaggt actacggcag
 541 aatcctgcac tacctgaagg ccaaagagta cagccactgc gcctggacca tcgtgagggt
 601 ggagatcctg cggaacttct acttcatcaa caggctgacc ggctacctga ggaacagctc
 661 cagcagcaag gcccctccac cctccctgcc ctccccaagc agactgcccg gaccctccga
 721 cacaccaatt ctgccacaga tgtcctacaa tctgctcgga tttctgcagc gctcctccaa
 781 ctttcagtgt cagaagctcc tctggcagct caatggccgc ctggaatatt gtctgaaaga
 841 cagaatgaat tttgacatcc cagaggaaat taaacagctc cagcagtttc agaaagaaga
 901 tgctgctctc acaatctatg aaatgctcca gaatatcttt gcaatctttc gccaggacag
 961 ctcctccacc gggtggaatg agacaattgt cgagaatctg ctcgccaatg tctatcatca
1021gatcaatcac ctcaagacag tcctcgaaga aaaactcgaa aaagaagatt tcacacgcgg
1081caaactgatg tcctccctgc atctgaagcg ctactatggg cgcatcctgc attatctgaa
1041agctaaagaa tactcccact gtgcttggac aattgtgcgc gtcgagatcc tgagaaactt
1101ttatttcatt aaccgcctga caggatacct gcgcaactga tgaaggtctg gatgcggccg
1161c
```

FIGURE 3E

Human Interferon-β 1a-MOD-9015

CTP-IFNβ 1A DNA and protein sequence

AA sequence (Accession No. NP_002167.1)

```
M  T  N  K  C  L  L  Q  I  A  L  L  L  C  F  S  T  T  A
L  S  S  S  S  S  K  A  P  P  P  S  L  P  S  P  S  R  L
P  G  P  S  D  T  P  I  L  P  Q  M  S  Y  N  L  L  G  F
L  Q  R  S  S  N  F  Q  C  Q  K  L  L  W  Q  L  N  G  R
L  E  Y  C  L  K  D  R  M  N  F  D  I  P  E  E  I  K  Q
L  Q  Q  F  Q  K  E  D  A  A  L  T  I  Y  E  M  L  Q  N
I  F  A  I  F  R  Q  D  S  S  S  T  G  W  N  E  T  I  V
E  N  L  L  A  N  V  Y  H  Q  I  N  H  L  K  T  V  L  E
E  K  L  E  K  E  D  F  T  R  G  K  L  M  S  S  L  H  L
K  R  Y  Y  G  R  I  L  H  Y  L  K  A  K  E  Y  S  H  C
A  W  T  I  V  R  V  E  I  L  R  N  F  Y  F  I  N  R  L
T  G  Y  L  R  N  *
```

Nucleotides Sequence (Accession No. NM_002176)

```
  1 tctagaggac atgaccaaca agtgcctgct gcagatcgcc ctgctgctgt gcttcagcac
 61 caccgccctg agcagcagca gctccaaggc ccccaccccc agcctgccca gcccagcag
121 gctgccaggc cccagcgaca ccccatcct gccccagatg agctacaacc tgctgggctt
181 cctgcagagg tccagcaact tccagtgcca gaaactgctg tggcagctga acggcaggct
241 ggaatactgc ctgaaggacc ggatgaactt cgacatcccc gaagagatca gcagctgca
301 gcagttccag aaagaggacg ccgccctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaaccgtg ctggaagaga gctggaaaa
481 agaggacttc accaggggca agctgatgag cagcctgcac ctgaagaggt actacggcag
541 aatcctgcac tacctgaagg ccaaagagta cagccactgc gcctggacca tcgtgagggt
601 ggagatcctg cggaacttct acttcatcaa caggctgacc ggctacctga ggaactgatg
661 agtccgcggc cgc
```

FIGURE 3F

Human Interferon-β 1a-MOD-9016

CTP-IFNβ 1A-CTP DNA and protein sequence

AA sequence (Accession No. NP_002167.1)

| M | T | N | K | C | L | L | Q | I | A | L | L | L | C | F | S | T | T | A |
|---|---|---|---|---|---|---|---|---|---|---|---|---|---|---|---|---|---|---|
| *L* | *S* | *S* | *S* | *S* | *S* | *K* | *A* | *P* | *P* | *P* | *S* | *L* | *P* | *S* | *P* | *S* | *R* | *L* |
| *P* | *G* | *P* | *S* | *D* | *T* | *P* | *I* | *L* | *P* | *Q* | M | S | Y | N | L | L | G | F |
| L | Q | R | S | S | N | F | Q | C | Q | K | L | L | W | Q | L | N | G | R |
| L | E | Y | C | L | K | D | R | M | N | F | D | I | P | E | E | I | K | Q |
| L | Q | Q | F | Q | K | E | D | A | A | L | T | I | Y | E | M | L | Q | N |
| I | F | A | I | F | R | Q | D | S | S | S | T | G | W | N | E | T | I | V |
| E | N | L | L | A | N | V | Y | H | Q | I | N | H | L | K | T | V | L | E |
| E | K | L | E | K | E | D | F | T | R | G | K | L | M | S | S | L | H | L |
| K | R | Y | Y | G | R | I | L | H | Y | L | K | A | K | E | Y | S | H | C |
| A | W | T | I | V | R | V | E | I | L | R | N | F | Y | F | I | N | R | L |
| T | G | Y | L | R | N | *S* | *S* | *S* | *S* | *K* | *A* | *P* | *P* | *P* | *S* | *L* | *P* | *S* |
| *P* | *S* | *R* | *L* | *P* | *G* | *P* | *S* | *D* | *T* | *P* | *I* | *L* | *P* | *Q* | * | | | |

Nucleotides Sequence (Accession No. NM_002176)

```
  1 tctagaggac atgaccaaca agtgcctgct gcagatcgcc ctgctgctgt gcttcagcac
 61 caccgccctg agcagcagca gctccaaggc ccacccccc agcctgccca gcccagcag
121 actgccaggc cccagcgaca cccccatcct gccccagatg agctacaacc tgctgggctt
181 cctgcagagg tccagcaact tccagtgcca gaagctgctg tggcagctga acggcaggct
241 ggaatactgc ctgaaggaca ggatgaactt cgacatccca gaggaaatca agcagctgca
301 gcagttccag aaggaggacg ccgccctgac catctacgag atgctgcaga acatcttcgc
361 catcttcagg caggacagca gcagcaccgg ctggaacgag accatcgtgg agaacctgct
421 ggccaacgtg taccaccaga tcaaccacct gaaaaccgtg ctggaagaga gctggaaaa
481 ggaggacttc accaggggca agctgatgag cagcctgcac ctgaagaggt actacgcag
541 aatcctgcac tacctgaagg ccaaggagta cagccactgc gcctggacca tcgtgagggt
601 ggagatcctg aggaacttct acttcatcaa caggctgacc ggctacctga ggaac*agctc*
661 *cagcagcaag gcccctccac cttccctgcc cagtccaagc cgactccctg ggccctccga*
721 *tacaccaatt ctgccacagt gatgaaggtc* tggatgcggc cgc
```

FIGURE 3G

SEQUENCE LISTING

<160> NUMBER OF SEQ ID NOS: 22

<210> SEQ ID NO 1
<211> LENGTH: 187
<212> TYPE: PRT
<213> ORGANISM: Homo sapiens

<400> SEQUENCE: 1

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser

```
                     85                  90                  95
Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
            130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185
```

<210> SEQ ID NO 2
<211> LENGTH: 840
<212> TYPE: DNA
<213> ORGANISM: Homo sapiens

<400> SEQUENCE: 2

```
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat cctacaaag aagcagcaat    180
tttcagtgtc agaagctcct gtggcaattg aatgggaggc ttgaatactg cctcaaggac   240
aggatgaact ttgacatccc tgaggagatt aagcagctgc agcagttcca gaaggaggac   300
gccgcattga ccatctatga gatgctccag aacatctttg ctattttcag acaagattca   360
tctagcactg gctggaatga actattgtt gagaaccctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta cagacttac aggttacctc cgaaactgaa gatctcctag cctgtgcctc   660
tgggactgga caattgcttc aagcattctt caaccagcag atgctgttta agtgactgat   720
ggctaatgta ctgcatatga aaggacacta gaagattttg aaatttttat taaattatga   780
gttatttta tttatttaaa ttttattttg gaaataaat tattttggt gcaaaagtca     840
```

<210> SEQ ID NO 3
<211> LENGTH: 211
<212> TYPE: PRT
<213> ORGANISM: Homo sapiens

<400> SEQUENCE: 3

```
Thr Phe Leu Gln Pro Phe Glu Ala Phe Ala Leu Ala Gln Gln Val Val
1               5                  10                  15

Gly Asp Thr Val Arg Val Val Asn Met Thr Asn Lys Cys Leu Leu Gln
            20                  25                  30

Ile Ala Leu Leu Leu Cys Phe Ser Thr Thr Ala Leu Ser Met Ser Tyr
        35                  40                  45

Asn Leu Leu Gly Phe Leu Gln Arg Ser Ser Asn Phe Gln Cys Gln Lys
    50                  55                  60

Leu Leu Trp Gln Leu Asn Gly Arg Leu Glu Tyr Cys Leu Lys Asp Arg
65                  70                  75                  80

Met Asn Phe Asp Ile Pro Glu Glu Ile Lys Gln Leu Gln Gln Phe Gln
```

```
                        85                  90                  95
Lys Glu Asp Ala Ala Leu Thr Ile Tyr Glu Met Leu Gln Asn Ile Phe
            100                 105                 110

Ala Ile Phe Arg Gln Asp Ser Ser Thr Gly Trp Asn Glu Thr Ile
            115                 120                 125

Val Glu Asn Leu Leu Ala Asn Val Tyr His Gln Ile Asn His Leu Lys
            130                 135                 140

Thr Val Leu Glu Glu Lys Leu Glu Lys Glu Asp Phe Thr Arg Gly Lys
145                 150                 155                 160

Leu Met Ser Ser Leu His Leu Lys Arg Tyr Tyr Gly Arg Ile Leu His
                165                 170                 175

Tyr Leu Lys Ala Lys Glu Tyr Ser His Cys Ala Trp Thr Ile Val Arg
            180                 185                 190

Val Glu Ile Leu Arg Asn Phe Tyr Phe Ile Asn Arg Leu Thr Gly Tyr
            195                 200                 205

Leu Arg Asn
    210

<210> SEQ ID NO 4
<211> LENGTH: 639
<212> TYPE: DNA
<213> ORGANISM: Homo sapiens

<400> SEQUENCE: 4
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat cctacaaag aagcagcaat    180 tttcagtgtc agaagctcct gtggcaattg aatgggaggc ttgaatactg cctcaaggac   240
aggatgaact tgacatccc tgaggagatt aagcagctgc agcagttcca gaaggaggac    300
gccgcattga ccatctatga gatgctccag aacatctttg ctattttcag acaagattca   360
tctagcactg gctggaatga gactattgtt gagaacctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta cagacttac aggttacctc cgaaactga                           639

<210> SEQ ID NO 5
<211> LENGTH: 215
<212> TYPE: PRT
<213> ORGANISM: Homo sapiens

<400> SEQUENCE: 5

Met Thr Asn Lys Cys Leu Leu Gln Ile Ala Leu Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
```

```
             85                  90                  95
Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
            115                 120                 125

Lys Glu Asp Phe Thr Arg Gly Lys Leu Met Ser Ser Leu His Leu Lys
            130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
                180                 185                 190

Ala Pro Pro Pro Ser Leu Pro Ser Pro Ser Arg Leu Pro Gly Pro Ser
                195                 200                 205

Asp Thr Pro Ile Leu Pro Gln
                210                 215
```

<210> SEQ ID NO 6
<211> LENGTH: 747
<212> TYPE: DNA
<213> ORGANISM: Homo sapiens

<400> SEQUENCE: 6

```
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctcttttccat gagctacaac ttgcttggat cctacaaag aagcagcaat   180
tttcagtgtc agaagctcct gtggcaattg aatgggaggc ttgaatactg cctcaaggac   240
aggatgaact tgacatccc tgaggagatt aagcagctgc agcagttcca gaaggaggac   300
gccgcattga ccatctatga gatgctccag aacatctttg ctatttcag acaagattca   360
tctagcactg gctggaatga gactattgtt gagaacctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta acagacttac aggttacctc cgaaactcct cttcctcaaa ggccccctccc   660
ccgagccttc caagtccatc ccgactcccg gggccctcgg acaccccgat cctcccacaa   720
taatgaagat ctcctagcct gtgcctc                                        747
```

<210> SEQ ID NO 7
<211> LENGTH: 243
<212> TYPE: PRT
<213> ORGANISM: Homo sapiens

<400> SEQUENCE: 7

```
Met Thr Asn Lys Cys Leu Leu Gln Ile Ala Leu Leu Leu Cys Phe Ser
1               5                  10                  15

Thr Thr Ala Leu Ser Met Ser Tyr Asn Leu Leu Gly Phe Leu Gln Arg
                20                 25                  30

Ser Ser Asn Phe Gln Cys Gln Lys Leu Leu Trp Gln Leu Asn Gly Arg
                35                 40                  45

Leu Glu Tyr Cys Leu Lys Asp Arg Met Asn Phe Asp Ile Pro Glu Glu
            50                  55                  60
```

```
Ile Lys Gln Leu Gln Gln Phe Gln Lys Glu Asp Ala Ala Leu Thr Ile
 65                  70                  75                  80

Tyr Glu Met Leu Gln Asn Ile Phe Ala Ile Phe Arg Gln Asp Ser Ser
                 85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Ser Ser Ser Ser Lys
            180                 185                 190

Ala Pro Pro Pro Ser Leu Pro Ser Pro Ser Arg Leu Pro Gly Pro Ser
        195                 200                 205

Asp Thr Pro Ile Leu Pro Gln Ser Ser Ser Lys Ala Pro Pro
    210                 215                 220

Ser Leu Pro Ser Pro Ser Arg Leu Pro Gly Pro Ser Asp Thr Pro Ile
225                 230                 235                 240

Leu Pro Gln
```

<210> SEQ ID NO 8
<211> LENGTH: 831
<212> TYPE: DNA
<213> ORGANISM: Homo sapiens

<400> SEQUENCE: 8

```
acattctaac tgcaaccttt cgaagccttt gctctggcac aacaggtagt aggcgacact    60
gttcgtgttg tcaacatgac caacaagtgt ctcctccaaa ttgctctcct gttgtgcttc   120
tccactacag ctctttccat gagctacaac ttgcttggat tcctacaaag aagcagcaat   180
tttcagtgtc agaagctcct gtggcaattg aatgggaggc ttgaatactg cctcaaggac   240
aggatgaact tgacatccc tgaggagatt aagcagctgc agcagttcca gaaggaggac   300
gccgcattga ccatctatga gatgctccag aacatctttg ctatttcag acaagattca   360
tctagcactg gctggaatga gactattgtt gagaaccctcc tggctaatgt ctatcatcag   420
ataaaccatc tgaagacagt cctggaagaa aaactggaga agaagatttt caccagggga   480
aaactcatga gcagtctgca cctgaaaaga tattatggga ggattctgca ttacctgaag   540
gccaaggagt acagtcactg tgcctggacc atagtcagag tggaaatcct aaggaacttt   600
tacttcatta acagacttac aggttacctc cgaaactcct cttcctcaaa ggcccctccc   660
ccgagccttc caagtccatc ccgactcccg gggccctcgg acacccccgat cctcccacaa   720
taatcctctt cctcaaaggc ccctcccccg agccttccaa gtccatcccg actcccgggg   780
ccctcggaca ccccgatcct cccacaatga agatctccta gcctgtgcct c            831
```

<210> SEQ ID NO 9
<211> LENGTH: 271
<212> TYPE: PRT
<213> ORGANISM: Homo sapiens

<400> SEQUENCE: 9

Met Thr Asn Lys Cys Leu Leu Gln Ile Ala Leu Leu Leu Cys Phe Ser

```
                1               5              10              15
Thr Thr Ala Leu Ser Ser Ser Ser Lys Ala Pro Pro Ser Leu
                20                      25                  30
Pro Ser Pro Ser Arg Leu Pro Gly Pro Ser Asp Thr Pro Ile Leu Pro
            35                      40                  45
Gln Met Ser Tyr Asn Leu Leu Gly Phe Leu Gln Arg Ser Ser Asn Phe
        50                      55                  60
Gln Cys Gln Lys Leu Leu Trp Gln Leu Asn Gly Arg Leu Glu Tyr Cys
65                      70                  75                  80
Leu Lys Asp Arg Met Asn Phe Asp Ile Pro Glu Glu Ile Lys Gln Leu
                    85                  90                  95
Gln Gln Phe Gln Lys Glu Asp Ala Ala Leu Thr Ile Tyr Glu Met Leu
                100                     105                 110
Gln Asn Ile Phe Ala Ile Phe Arg Gln Asp Ser Ser Ser Thr Gly Trp
            115                     120                 125
Asn Glu Thr Ile Val Glu Asn Leu Leu Ala Asn Val Tyr His Gln Ile
        130                     135                 140
Asn His Leu Lys Thr Val Leu Glu Glu Lys Leu Glu Lys Glu Asp Phe
145                     150                 155                 160
Thr Arg Gly Lys Leu Met Ser Ser Leu His Leu Lys Arg Tyr Tyr Gly
                    165                 170                 175
Arg Ile Leu His Tyr Leu Lys Ala Lys Glu Tyr Ser His Cys Ala Trp
                180                 185                 190
Thr Ile Val Arg Val Glu Ile Leu Arg Asn Phe Tyr Phe Ile Asn Arg
            195                 200                 205
Leu Thr Gly Tyr Leu Arg Asn Ser Ser Ser Lys Ala Pro Pro
        210                 215                 220
Ser Leu Pro Ser Pro Ser Arg Leu Pro Gly Pro Ser Asp Thr Pro Ile
225                 230                 235                 240
Leu Pro Gln Ser Ser Ser Lys Ala Pro Pro Ser Leu Pro Ser
                245                 250                 255
Pro Ser Arg Leu Pro Gly Pro Ser Asp Thr Pro Ile Leu Pro Gln
            260                 265                 270
```

<210> SEQ ID NO 10
<211> LENGTH: 915
<212> TYPE: DNA
<213> ORGANISM: Homo sapiens

<400> SEQUENCE: 10

```
acattctaac tgcaaccttt cgaagccttt gctctggcac aacaggtagt aggcgacact      60
gttcgtgttg tcaacatgac caacaagtgt ctcctccaaa ttgctctcct gttgtgcttc    120
tccactacag ctctttcctc ctcttcctca aaggcccctc ccccgagcct tccaagtcca    180
tcccgactcc cggggccctc ggacaccccg atcctcccac aaatgagcta caacttgctt    240
ggattcctac aaagaagcag caattttcag tgtcagaagc tcctgtggca attgaatggg    300
aggcttgaat actgcctcaa ggacaggatg aactttgaca tccctgagga gattaagcag    360
ctgcagcagt tccagaagga ggacgccgca ttgaccatct atgagatgct ccagaacatc    420
tttgctattt tcagacaaga ttcatctagc actggctgga atgagactat tgttgagaac    480
ctcctggcta atgtctatca tcagataaac catctgaaga cagtcctgga agaaaaactg    540
gagaagaag atttcaccag ggaaaaactc atgagcagtc tgcacctgaa aagatattat    600
gggaggattc tgcattacct gaaggccaag gagtacagtc actgtgcctg gaccatagtc    660
```

```
agagtggaaa tcctaaggaa cttttacttc attaacagac ttacaggtta cctccgaaac    720
tcctcttcct caaaggcccc tcccccgagc cttccaagtc catcccgact cccggggccc    780
tcggacaccc cgatcctccc acaataatcc tcttcctcaa aggcccctcc cccgagcctt    840
ccaagtccat cccgactccc ggggccctcg acaccccga tcctcccaca atgaagatct    900
cctagcctgt gcctc    915
```

<210> SEQ ID NO 11
<211> LENGTH: 409
<212> TYPE: PRT
<213> ORGANISM: Homo sapiens

<400> SEQUENCE: 11

```
Met Thr Asn Lys Cys Leu Leu Gln Ile Ala Leu Leu Leu Cys Phe Ser
1               5                   10                  15

Thr Thr Ala Leu Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
        35                  40                  45

Gln Met Ser Tyr Asn Leu Leu Gly Phe Leu Gln Arg Ser Ser Asn Phe
    50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
        115                 120                 125

Asn Glu Thr Ile Val Glu Asn Leu Leu Ala Asn Val Tyr His Gln Ile
130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
        195                 200                 205

Leu Thr Gly Tyr Leu Arg Asn Ser Ser Ser Lys Ala Pro Pro Pro
    210                 215                 220

Ser Leu Pro Ser Pro Ser Arg Leu Pro Gly Pro Ser Asp Thr Pro Ile
225                 230                 235                 240

Leu Pro Gln Met Ser Tyr Asn Leu Leu Gly Phe Leu Gln Arg Ser Ser
                245                 250                 255

Asn Phe Gln Cys Gln Lys Leu Leu Trp Gln Leu Asn Gly Arg Leu Glu
            260                 265                 270

Tyr Cys Leu Lys Asp Arg Met Asn Phe Asp Ile Pro Glu Glu Ile Lys
        275                 280                 285

Gln Leu Gln Gln Phe Gln Lys Glu Asp Ala Ala Leu Thr Ile Tyr Glu
    290                 295                 300

Met Leu Gln Asn Ile Phe Ala Ile Phe Arg Gln Asp Ser Ser Ser Thr
305                 310                 315                 320

Gly Trp Asn Glu Thr Ile Val Glu Asn Leu Leu Ala Asn Val Tyr His
                325                 330                 335
```

```
Gln Ile Asn His Leu Lys Thr Val Leu Glu Glu Lys Leu Glu Lys Glu
            340                 345                 350

Asp Phe Thr Arg Gly Lys Leu Met Ser Ser Leu His Leu Lys Arg Tyr
            355                 360                 365

Tyr Gly Arg Ile Leu His Tyr Leu Lys Ala Lys Glu Tyr Ser His Cys
        370                 375                 380

Ala Trp Thr Ile Val Arg Val Glu Ile Leu Arg Asn Phe Tyr Phe Ile
385                 390                 395                 400

Asn Arg Leu Thr Gly Tyr Leu Arg Asn
            405

<210> SEQ ID NO 12
<211> LENGTH: 1326
<212> TYPE: DNA
<213> ORGANISM: Homo sapiens

<400> SEQUENCE: 12
acattctaac tgcaaccttt cgaagccttt gctctggcac aacaggtagt aggcgacact      60
gttcgtgttg tcaacatgac caacaagtgt ctcctccaaa ttgctctcct gttgtgcttc    120
tccactacag ctctttcctc ctcttcctca aggcccctc ccccgagcct tccaagtcca     180
tcccgactcc cggggccctc ggacaccccg atcctcccac aaatgagcta caacttgctt    240
ggattcctac aaagaagcag caattttcag tgtcagaagc tcctgtggca attgaatggg    300
aggcttgaat actgcctcaa ggacaggatg aactttgaca tccctgagga gattaagcag    360
ctgcagcagt tccagaagga ggacgccgca ttgaccatct atgagatgct ccagaacatc    420
tttgctattt tcagacaaga ttcatctagc actggctgga atgagactat tgttgagaac    480
ctcctggcta atgtctatca tcagataaac catctgaaga cagtcctgga agaaaaactg    540 gagaagaag atttcaccag gggaaaactc atgagcagtc tgcacctgaa agatattat     600 gggaggattc tgcattacct gaaggccaag gagtacagtc actgtgcctg gaccatagtc    660
agagtggaaa tcctaaggaa cttttacttc attaacagac ttacaggtta cctccgaaac    720
tcctcttcct caaaggcccc tcccccgagc cttccaagtc catcccgact cccggggccc    780
tcggacaccc cgatcctccc acaaatgagc tacaacttgc ttggattcct acaaagaagc    840
agcaattttc agtgtcagaa gctcctgtgg caattgaatg gaggcttga atactgcctc    900 aaggacagga tgaactttga catccctgag gagattaagc agctgcagca gttccagaag    960
gaggacgccg cattgaccat ctatgagatg ctccagaaca tctttgctat tttcagacaa   1020
gattcatcta gcactggctg gaatgagact attgttgaga acctcctggc taatgtctat   1080
catcagataa accatctgaa gacagtcctg gaagaaaaac tggagaaaga gatttcacc   1140 aggggaaaac tcatgagcag tctgcacctg aaaagatatt atgggaggat ctgcattac   1200 ctgaaggcca aggagtacag tcactgtgcc tggaccatag tcagagtgga aatcctaagg   1260 aactttttact tcattaacag acttacaggt tacctccgaa actgaagatc tcctagcctg   1320
tgcctc                                                              1326

<210> SEQ ID NO 13
<211> LENGTH: 215
<212> TYPE: PRT
<213> ORGANISM: Homo sapiens

<400> SEQUENCE: 13

Met Thr Asn Lys Cys Leu Leu Gln Ile Ala Leu Leu Leu Cys Phe Ser
1               5                   10                  15
```

```
Thr Thr Ala Leu Ser Ser Ser Ser Lys Ala Pro Pro Ser Leu
        20                  25                  30

Pro Ser Pro Ser Arg Leu Pro Gly Pro Ser Asp Thr Pro Ile Leu Pro
            35                  40                  45

Gln Met Ser Tyr Asn Leu Leu Gly Phe Leu Gln Arg Ser Ser Asn Phe
    50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Ser Thr Gly Trp
        115                 120                 125

Asn Glu Thr Ile Val Glu Asn Leu Leu Ala Asn Val Tyr His Gln Ile
    130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
        195                 200                 205

Leu Thr Gly Tyr Leu Arg Asn
    210                 215

<210> SEQ ID NO 14
<211> LENGTH: 744
<212> TYPE: DNA
<213> ORGANISM: Homo sapiens

<400> SEQUENCE: 14
acattctaac tgcaaccttt cgaagccttt gctctggcac aacaggtagt aggcgacact      60
gttcgtgttg tcaacatgac caacaagtgt ctcctccaaa ttgctctcct gttgtgcttc     120
tccactacag ctctttcctc ctcttcctca aggcccctc ccccgagcct tccaagtcca      180
tcccgactcc cggggccctc ggacaccccg atcctcccac aaatgagcta caacttgctt     240
ggattcctac aaagaagcag caattttcag tgtcagaagc tcctgtggca attgaatggg     300
aggcttgaat actgcctcaa ggacaggatg aactttgaca tccctgagga gattaagcag     360
ctgcagcagt tccagaagga ggacgccgca ttgaccatct atgagatgct ccagaacatc     420
tttgctattt tcagacaaga ttcatctagc actggctgga atgagactat tgttgagaac     480
ctcctggcta atgtctatca tcagataaac catctgaaga cagtcctgga agaaaaactg     540 gagaagaag atttcaccag gggaaaactc atgagcagtc tgcacctgaa aagatattat     600
gggaggattc tgcattacct gaaggccaag gagtacagtc actgtgcctg gaccatagtc     660
agagtggaaa tcctaaggaa cttttacttc attaacagac ttacaggtta cctccgaaac     720
tgaagatctc ctagcctgtg cctc                                            744

<210> SEQ ID NO 15
<211> LENGTH: 243
<212> TYPE: PRT
<213> ORGANISM: Homo sapiens
```

```
<400> SEQUENCE: 15

Met Thr Asn Lys Cys Leu Leu Gln Ile Ala Leu Leu Leu Cys Phe Ser
1               5                   10                  15

Thr Thr Ala Leu Ser Ser Ser Ser Lys Ala Pro Pro Pro Ser Leu
            20                  25                  30

Pro Ser Pro Ser Arg Leu Pro Gly Pro Ser Asp Thr Pro Ile Leu Pro
            35                  40                  45

Gln Met Ser Tyr Asn Leu Leu Gly Phe Leu Gln Arg Ser Ser Asn Phe
    50                  55                  60

Gln Cys Gln Lys Leu Leu Trp Gln Leu Asn Gly Arg Leu Glu Tyr Cys
65                  70                  75                  80

Leu Lys Asp Arg Met Asn Phe Asp Ile Pro Glu Glu Ile Lys Gln Leu
                85                  90                  95

Gln Gln Phe Gln Lys Glu Asp Ala Ala Leu Thr Ile Tyr Glu Met Leu
            100                 105                 110

Gln Asn Ile Phe Ala Ile Phe Arg Gln Asp Ser Ser Thr Gly Trp
            115                 120                 125

Asn Glu Thr Ile Val Glu Asn Leu Leu Ala Asn Val Tyr His Gln Ile
130                 135                 140

Asn His Leu Lys Thr Val Leu Glu Glu Lys Leu Glu Lys Glu Asp Phe
145                 150                 155                 160

Thr Arg Gly Lys Leu Met Ser Ser Leu His Leu Lys Arg Tyr Tyr Gly
                165                 170                 175

Arg Ile Leu His Tyr Leu Lys Ala Lys Glu Tyr Ser His Cys Ala Trp
            180                 185                 190

Thr Ile Val Arg Val Glu Ile Leu Arg Asn Phe Tyr Phe Ile Asn Arg
            195                 200                 205

Leu Thr Gly Tyr Leu Arg Asn Ser Ser Ser Lys Ala Pro Pro
    210                 215                 220

Ser Leu Pro Ser Pro Ser Arg Leu Pro Gly Pro Ser Asp Thr Pro Ile
225                 230                 235                 240

Leu Pro Gln

<210> SEQ ID NO 16
<211> LENGTH: 828
<212> TYPE: DNA
<213> ORGANISM: Homo sapiens

<400> SEQUENCE: 16
acattctaac tgcaaccttt cgaagccttt gctctggcac aacaggtagt aggcgacact      60
gttcgtgttg tcaacatgac caacaagtgt ctcctccaaa ttgctctcct gttgtgcttc    120
tccactacag ctctttcctc ctcttcctca aggccccctc cccgagcctt ccaagtcca     180 tcccgactcc cggggccctc ggacacccg atcctcccac aaatgagcta caacttgctt     240
ggattcctac aaagaagcag caattttcag tgtcagaagc tcctgtggca attgaatggg    300
aggcttgaat actgcctcaa ggacaggatg aactttgaca tccctgagga gattaagcag    360
ctgcagcagt tccagaagga ggacgccgca ttgaccatct atgagatgct ccagaacatc    420
tttgctattt tcagacaaga ttcatctagc actggctgga atgagactat tgttgagaac    480
ctcctggcta atgtctatca tcagataaac catctgaaga cagtcctgga agaaaaactg    540
gagaaagaag atttcaccag ggaaaactc atgagcagtc tgcacctgaa aagatattat    600
gggaggattc tgcattacct gaaggccaag gagtacagtc actgtgcctg gaccatagtc    660
agagtggaaa tcctaaggaa cttttacttc attaacagac ttacaggtta cctccgaaac    720
```
tcctcttcct caaaggcccc tcccccgagc cttccaagtc catcccgact cccggggccc    780
tcggacaccc cgatcctccc acaatgaaga tctcctagcc tgtgcctc                 828

<210> SEQ ID NO 17
<211> LENGTH: 165
<212> TYPE: PRT
<213> ORGANISM: Homo sapiens

<400> SEQUENCE: 17

Met Ser Tyr Asn Leu Leu Gly Phe Leu Gln Arg Ser Ser Asn Phe Gln
1               5                   10                  15

Ser Gln Lys Leu Leu Trp Gln Leu Asn Gly Arg Leu Glu Tyr Cys Leu
            20                  25                  30

Lys Asp Arg Met Asn Phe Asp Ile Pro Glu Glu Ile Lys Gln Leu Gln
        35                  40                  45

Gln Phe Gln Lys Glu Asp Ala Ala Leu Thr Ile Tyr Glu Met Leu Gln
    50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
    130                 135                 140

Ile Val Arg Val Glu Ile Leu Arg Asn Phe Tyr Phe Ile Asn Arg Leu
145                 150                 155                 160

Thr Gly Tyr Leu Arg
                165

<210> SEQ ID NO 18
<211> LENGTH: 28
<212> TYPE: PRT
<213> ORGANISM: Homo sapiens

<400> SEQUENCE: 18

Ser Ser Ser Ser Lys Ala Pro Pro Pro Ser Leu Pro Ser Pro Ser Arg
1               5                   10                  15

Leu Pro Gly Pro Ser Asp Thr Pro Ile Leu Pro Gln
            20                  25

<210> SEQ ID NO 19
<211> LENGTH: 21
<212> TYPE: PRT
<213> ORGANISM: Homo sapiens

<400> SEQUENCE: 19

Met Thr Asn Lys Cys Leu Leu Gln Ile Ala Leu Leu Leu Cys Phe Ser
1               5                   10                  15

Thr Thr Ala Leu Ser
            20

<210> SEQ ID NO 20
<211> LENGTH: 23
<212> TYPE: DNA
<213> ORGANISM: Homo sapiens

```
<400> SEQUENCE: 20
gaattctaga ggacatgacc aac                                               23

<210> SEQ ID NO 21
<211> LENGTH: 33
<212> TYPE: DNA
<213> ORGANISM: Homo sapiens

<400> SEQUENCE: 21
gcggccgcgg actcatcagt tcctcaggta gcc                                    33

<210> SEQ ID NO 22
<211> LENGTH: 12
<212> TYPE: PRT
<213> ORGANISM: Homo sapiens

<400> SEQUENCE: 22

Ser Ser Ser Ser Lys Ala Pro Pro Pro Ser Leu Pro
1               5                   10
```

LONG-ACTING INTERFERONS AND DERIVATIVES THEREOF AND METHODS THEREOF

CROSS REFERENCE TO RELATED APPLICATIONS

This application is a continuation-in-part of U.S. patent application Ser. No. 11/700,911, filed Feb. 1, 2007, now U.S. Pat. No. 7,553,941, which claims priority of U.S. Provisional Application Ser. No. 60/764,761, filed Feb. 3, 2006, which is hereby incorporated in its entirety by reference herein

FIELD OF INVENTION

A polypeptide and polynucleotides encoding same comprising at least two carboxy-terminal peptides (CTP) of chorionic gonadotrophin attached to an IFN protein are disclosed. Pharmaceutical compositions comprising the polypeptide and polynucleotides of the invention and methods of using same are also disclosed.

BACKGROUND OF THE INVENTION

Polypeptides are susceptible to denaturation or enzymatic degradation in the blood, liver or kidney. Accordingly, polypeptides typically have short circulatory half-lives of several hours. Because of their low stability, peptide drugs are usually delivered in a sustained frequency so as to maintain an effective plasma concentration of the active peptide. Moreover, since peptide drugs are usually administrated by infusion, frequent injection of peptide drugs cause considerable discomfort to a subject. Thus, there is a need for technologies that will prolong the half-lives of therapeutic polypeptides while maintaining a high pharmacological efficacy thereof. Such desirous peptide drugs should also meet the requirements of enhanced serum stability, high activity and a low probability of inducing an undesired immune response when injected into a subject.

Unfavorable pharmacokinetics, such as a short serum half-life, can prevent the pharmaceutical development of many otherwise promising drug candidates. Serum half-life is an empirical characteristic of a molecule, and must be determined experimentally for each new potential drug. For example, with lower molecular weight polypeptide drugs, physiological clearance mechanisms such as renal filtration can make the maintenance of therapeutic levels of a drug unfeasible because of cost or frequency of the required dosing regimen. Conversely, a long serum half-life is undesirable where a drug or its metabolites have toxic side effects.

Interferons (IFNs) are a family of functionally related cytokines that exhibit antiviral, antiproliferative and immunomodulatory activities. They are divided into two groups, designated type I and type II IFNs. The type I IFNs include the IFN-α family (e.g. IFN-α2a, IFN-α2b, IFN-αn3, and IFN-αcon-1), IFN-β and IFN-omega. They are all structurally related and compete for the same cell surface receptor. Type I interferons are produced in many cell types upon infection by a variety of viruses. IFN-γ is the sole member of the type II IFNs. It is acid labile, binds to its own specific receptor and is produced by activated T cells and NK cells.

Type I and Type II IFNs have overlapping but clearly distinct biological activities. Type I IFNs induce antiproliferative and antiviral activity, while type II IFN-γ has weaker antiviral activity but more potent immunomodulatory properties. IFN-γ exhibits also immune functions, including macrophage activation.

SUMMARY OF THE INVENTION

In one embodiment, the present invention provides a polypeptide comprising an interferon (IFN) protein and at least one chorionic gonadotrophin carboxy terminal peptide (CTP) attached to an amino terminus of an interferon protein and at least two chorionic gonadotrophin carboxy terminal peptides attached to a carboxy terminus of an interferon protein.

In another embodiment, the present invention further provides a polynucleotide comprising a coding portion encoding a polypeptide, wherein the polypeptide comprises an interferon (IFN) protein and at least one chorionic gonadotrophin carboxy terminal peptide (CTP) attached to an amino terminus of an interferon protein and at least two chorionic gonadotrophin carboxy terminal peptides attached to a carboxy terminus of an interferon protein.

In another embodiment, the present invention further provides a method of improving a biological half life of an interferon (IFN) protein, comprising the step of attaching at least one chorionic gonadotrophin carboxy terminal peptide to an amino terminus of an interferon (IFN) protein and at least two chorionic gonadotrophin carboxy terminal peptide to a carboxy terminus of an IFN protein, thereby improving a biological half life of an interferon (IFN) protein.

BRIEF DESCRIPTION OF THE DRAWINGS

FIG. 3 MOD-9010 (A), MOD-9011 (B), MOD-9012 (C), MOD-9013 (D), MOD-9014 (E), MOD-9015 (F), and MOD-9016 (G) amino acid sequences (AA) followed by DNA sequences. Underline: Signal sequence, Black letters: Mature protein, Italic: CTP unit.

DETAILED DESCRIPTION OF THE INVENTION

Figure 1:
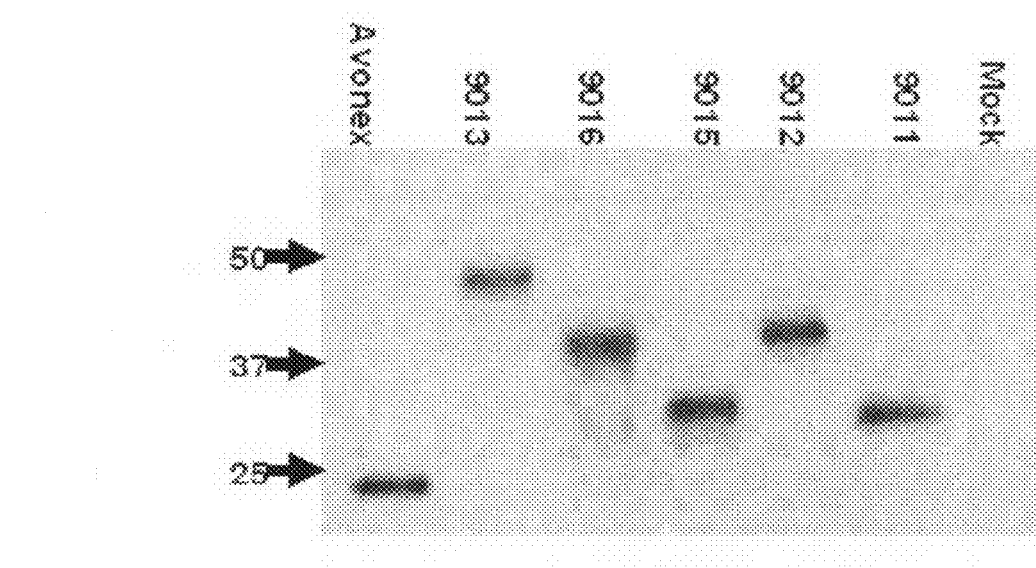
FIG. 1 is a Western blot illustrating the molecular weight & identity of Avonex, MOD-9013 (SEQ ID NO: 9), MOD-9016 (SEQ ID NO: 15), MOD-9015 (SEQ ID NO: 13), MOD-9012 (SEQ ID NO: 7), MOD-9011 (SEQ ID NO: 5) and Mock. PAGE SDS gel was blotted and stained using monoclonal anti-IFN-β1A antibodies (B). The photograph indicates that like commercial Avonex, MOD-901X variants are recognized by anti IFN-β1A antibodies.

In one embodiment, the present invention provides long-acting polypeptides and methods of producing and using same. In another embodiment, long-acting polypeptides comprise carboxy terminal peptide (CTP, also referred to as CTP unit) and an interferon (IFN) protein. In another embodiment, long-acting polypeptides comprise carboxy terminal peptide (CTP) and human interferon (IFN) protein. In another embodiment, CTP acts as a protectant against degradation of proteins or peptides. In another embodiment, CTP extends circulatory half-lives of proteins or peptides. In some embodiments, CTP enhances the potency of proteins or peptides.

In another embodiment, the present invention provides a polypeptide comprising an interferon (IFN) protein and at least one chorionic gonadotrophin carboxy terminal peptide (CTP) attached to an amino terminus of an interferon protein and at least two chorionic gonadotrophin carboxy terminal peptides attached to a carboxy terminus of an interferon protein. In another embodiment, the present invention provides a polypeptide comprising one chorionic gonadotrophin carboxy terminal peptide attached to an amino terminus of an interferon protein and two chorionic gonadotrophin carboxy terminal peptides attached to a carboxy terminus of an interferon protein.

In another embodiment, "CTP peptide," "carboxy terminal peptide" and "CTP sequence" are used interchangeably herein. In another embodiment, the carboxy terminal peptide is a full-length CTP. In another embodiment, the carboxy terminal peptide is a truncated CTP. Each possibility represents a separate embodiment of the present invention.

In another embodiment, "signal sequence" and "signal peptide" are used interchangeably herein. In another embodiment, "sequence" when in reference to a polynucleotide can refer to a coding portion. Each possibility represents a separate embodiment of the present invention.

In another embodiment, "peptide of interest" and "polypeptide sequence-of-interest" are used interchangeably herein. In another embodiment, the peptide of interest is a full-length protein. In another embodiment, the peptide of interest is a protein fragment. Each possibility represents a separate embodiment of the present invention. In another embodiment, the peptide of interest is an interferon protein.

In another embodiment, the carboxy-terminal peptide (CTP) sequence is of human chorionic gonadotrophin. In another embodiment, the carboxy-terminal peptide (CTP) is attached to the polypeptide sequence of interest via a linker. In another embodiment, the linker which connects the CTP sequence to the polypeptide sequence of interest is a covalent bond. In another embodiment, the linker which connects the CTP sequence to the polypeptide sequence of interest is a peptide bond. In another embodiment, the linker which connects the CTP sequence to the polypeptide sequence of interest is a substituted peptide bond. In another embodiment, the carboxy-terminal peptide (CTP) sequence comprises an amino acid sequence selected from the sequences set forth in SEQ ID NO: 17 and SEQ ID NO: 18.

In another embodiment, SEQ ID NO: 17 comprise the following amino acid (AA) sequence: DPRFQDSSSSKAP-PPSLPSPSRLPGPSDTPIL (SEQ ID NO: 17). In another embodiment, SEQ ID NO: 18 comprise the following amino acid (AA) sequence:

SSSSKAPPPSLPSPSRLPGPSDTPILPQ.  (SEQ ID NO: 18)

In another embodiment, at least one carboxy-terminal peptide (CTP) sequence comprises an amino acid sequence selected from the sequences set forth in SEQ ID NO: 17 and SEQ ID NO: 18. In another embodiment, at least one carboxy-terminal peptide (CTP) is glycosylated. In another embodiment, at least one carboxy-terminal peptide (CTP) is truncated.

In another embodiment, the polypeptide of the present invention further comprises a signal peptide for the secretion of the polypeptides of the present invention. In some embodiments, signal sequences include, but are not limited to the endogenous signal sequence for IFN. In another embodiment, the polypeptides and methods of the present invention provide an IFN protein having additionally a signal peptide of SEQ ID NO: 19 and at least one CTP peptide on the N-terminus and at least one CTP peptide on the C-terminus. In another embodiment, the polypeptides and methods of the present invention provide an IFN protein having additionally on the N-terminus the signal peptide of SEQ ID NO: 19 and at least one CTP peptide on the N-terminus and at least two CTP peptides on the C-terminus. In another embodiment, the polypeptides and methods of the present invention provide an IFN protein having additionally on the N-terminus the signal peptide of SEQ ID NO: 19 and a single CTP peptide on the N-terminus and two CTP peptides on the C-terminus. In another embodiment, SEQ ID NO: 19 comprise the following amino acid (AA) sequence: MTNKCLLQIALLLCFST-TALS (SEQ ID NO: 19).

In another embodiment, the interferon (IFN) is a type I interferon. In another embodiment, the interferon (IFN) is IFN-α In another embodiment, the interferon (IFN) is IFN-β In another embodiment, the interferon (IFN) is IFN-γ. In another embodiment, an interferon (IFN) peptide as described herein comprises an amino acid sequence as described herein including the sequences provided in FIG. 3. In another embodiment, a polypeptide of the invention comprising interferon (IFN) peptide and at least one CTP unit attached to an amino and/or a carboxy terminus of the polypeptide as described herein comprises an amino acid sequence as described herein including the sequences provided in FIG. 3. In another embodiment, an interferon (IFN) peptide as described herein comprises an amino acid sequence set forth in SEQ ID NO: 1. In another embodiment, SEQ ID NO: 1 comprises the following amino acid (AA) sequence:

MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRN
(SEQ ID NO: 1, Human Interferon-β 1a-MOD-9010).

In another embodiment, an interferon (IFN) peptide as described herein comprises an amino acid sequence of human interferon β1a (hIFN β1a). In another embodiment, an interferon (IFN) peptide as described herein comprises an amino acid sequence set fourth in GenBank Accession No. NP_002167.1.

In another embodiment, an interferon (IFN) peptide as described herein is encoded by a nucleotide acid sequence set forth in SEQ ID NO: 2. In another embodiment, SEQ ID NO: 2 comprises the following nucleotide acid (NA) sequence:

(SEQ ID NO: 2, Human Interferon-β1a-MOD-9010)
tctagaggacatgaccaacaagtgcctgctgcagatcgccctgctgctgt gcttcagcaccaccgccctgagcatgagctacaacctgctgggcttcctg cagaggtccagcaacttccagtgccagaagctgctgtggcagctgaacgg caggctggaatactgcctgaaggacaggatgaacttcgacatcccagagg aaatcaagcagctgcagcagttccagaaggaggacgccgccctgaccatc tacgagatgctgcagaacatcttcgccatcttcaggcaggacagcagcag caccggctggaacgagaccatcgtggagaacctgctggccaacgtgtacc accagatcaaccacctgaaaaccgtgctggaagagaagctggaaaaggag -continued
```
gacttcaccaggggcaagctgatgagcagcctgcacctgaagaggtacta cggcagaatcctgcactacctgaaggccaaggagtacagccactgcgcct ggaccatcgtgagggtggagatcctgaggaacttctacttcatcaacagg ctgaccggctacctgaggaactgatgagtccgcggccgc.
```

In another embodiment, an interferon (IFN) peptide as described herein is encoded by a nucleotide acid (NA) molecule of human interferon β1a (hIFN β1a). In another embodiment, an interferon (IFN) peptide as described herein is encoded by a nucleotide acid (NA) molecule comprising a nucleotide acid sequence set fourth in GenBank Accession No. NM_002176.

In another embodiment, an interferon (IFN) peptide as described herein comprises an amino acid sequence set forth in SEQ ID NO: 3. In another embodiment, SEQ ID NO: 3 comprises the following amino acid (AA) sequence:

```
                                          (SEQ ID NO: 3)
TF*LQPFEAFALAQQVVGDTVRVVNMTNKCLLQIALLLCFSTTALSMSYN

LLGFLQRSSNFQCQKLLWQLNGRLEYCLKDRMNFDIPEEIKQLQQFQKED

AALTIYEMLQNIFAIFRQDSSSTGWNETIVENLLANVYHQINHLKTVLEE

KLEKEDFTRGKLMSSLHLKRYYGRILHYLKAKEYSHCAWTIVRVEILRNF

YFINRLTGYLRN.
```

In another embodiment, an interferon (IFN) peptide as described herein is encoded by a nucleotide acid sequence set forth in SEQ ID NO: 4. In another embodiment, SEQ ID NO: 2 comprises the following nucleotide acid (NA) sequence:

```
                                          (SEQ ID NO: 4)
acattctaactgcaaccttttcgaagcctttgctctggcacaacaggtagt aggcgacactgttcgtgttgtcaacatgaccaacaagtgtctcctccaaa ttgctctcctgttgtgcttctccactacagctctttccatgagctacaac ttgcttggattcctacaaagaagcagcaattttcagtgtcagaagctcct gtggcaattgaatgggaggcttgaatactgcctcaaggacaggatgaact ttgacatccctgaggagattaagcagctgcagcagttccagaaggaggac gccgcattgaccatctatgagatgctccagaacatctttgctattttcag acaagattcatctagcactggctgaatgagactattgttgagaacctcc tggctaatgtctatcatcagataaaccatctgaagacagtcctggaagaa aaactggagaaagaagattcaccaggggaaaactcatgagcagtctgca cctgaaaagatattatgggaggattctgcattacctgaaggccaaggagt acagtcactgtgcctggaccatagtcagagtggaaatcctaaggaactttt tacttcattaacagacttacaggttacctccgaaactga.
```

In another embodiment, the polypeptide as described herein comprises an interferon (IFN) peptide and a CTP unit. In another embodiment, the polypeptide as described herein comprises an interferon (IFN) peptide and a CTP unit attached to the carboxy terminus. In another embodiment, the polypeptide as described herein comprises an interferon (IFN) peptide and at least one CTP unit attached to the carboxy terminus. In another embodiment, the polypeptide as described herein comprises an interferon (IFN) peptide and a CTP unit attached to the amino terminus. In another embodiment, the polypeptide as described herein comprises an interferon (IFN) peptide and at least one CTP unit attached to the amino terminus. In another embodiment, the polypeptide as described herein comprises an interferon (IFN) peptide, at least one CTP unit attached to the amino terminus, and at least one CTP unit attached to the carboxy terminus. In another embodiment, the polypeptide as described herein comprises an interferon (IFN) peptide, at least one CTP unit attached to the amino terminus, and two CTP units in tandem attached to the carboxy terminus. In another embodiment, the polypeptide as described herein comprises an interferon (IFN) peptide, at least one CTP unit attached to the amino terminus, and two CTP units attached to the carboxy terminus. In another embodiment, the polypeptide as described herein comprises an interferon (IFN) peptide, one CTP unit attached to the amino terminus, and at least two CTP units attached to the carboxy terminus. In another embodiment, the polypeptide as described herein comprises an interferon (IFN) peptide, one CTP unit attached to the amino terminus, and two CTP units attached to the carboxy terminus. In another embodiment, the polypeptide as described herein comprises an interferon (IFN) peptide, one CTP unit attached to the amino terminus, and at least two CTP units attached to the carboxy terminus. In another embodiment, the polypeptide as described herein comprises an interferon (IFN) peptide, one CTP unit attached to the amino terminus, and at least two CTP units in tandem attached to the carboxy terminus.

In another embodiment, the polypeptide as described herein comprises an interferon (IFN) peptide and at least three CTP units. In another embodiment, the polypeptide as described herein comprises an interferon (IFN) peptide and three CTP units. In another embodiment, the polypeptide as described herein comprises an interferon (IFN) peptide-CTP polypeptide encoded by an amino acid sequence comprising the amino acid sequence set forth in SEQ ID NO: 5. In another embodiment, SEQ ID NO: 5 comprises the following amino acid (AA) sequence:

```
                                 (SEQ ID NO: 5, MOD-9011)
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRNSSSSKAPPPSLPS

PSRLPGPSDTPILPQ.
```

In another embodiment, the polypeptide as described herein comprising an interferon (IFN) peptide- and CTP is encoded by a nucleic acid molecule set forth in SEQ ID NO: 6. In another embodiment, SEQ ID NO: 6 comprises the following nucleotide acid (NA) sequence:

```
                                 (SEQ ID NO: 6, MOD-9011)
tctagaggacatgaccaacaagtgcctgctgcagatcgccctgctgctgt gcttcagcaccaccgccctgagcatgagctacaacctgctgggcttcctg cagaggtccagcaacttccagtgccagaagctgctgtggcagctgaacgg caggctggaatactgcctgaaggacaggatgaacttcgacatcccagagg aaatcaagcagctgcagcagttccagaaggaggacgccgccctgaccatc tacgagatgctgcagaacatcttcgccatcttcaggcaggacagcagcag caccggctggaacgagaccatcgtggagaacctgctggccaacgtgtacc
```

-continued

```
accagatcaaccacctgaaaaccgtgctggaagagaagctggaaaaggag gacttcaccaggggcaagctgatgagcagcctgcacctgaagaggtacta cggcagaatcctgcactacctgaaggccaaggagtacagccactgcgcct ggaccatcgtgagggtggagatcctgaggaacttctacttcatcaacagg ctgaccggctacctgaggaacagctccagcagcaaggcccctccaccttc cctgcccagtccaagccgactccctgggccctccgatacaccaatcctgc cacagtgatga.
```

In another embodiment, the polypeptide as described herein comprises an interferon (IFN) peptide and two CTP units attached to its carboxy terminus. In another embodiment, the polypeptide as described herein comprises an interferon (IFN) peptide-CTP (x2) encoded by an amino acid sequence comprising the amino acid sequence set forth in SEQ ID NO: 7. In another embodiment, SEQ ID NO: 7 comprises the following amino acid (AA) sequence:

```
                           (SEQ ID NO: 7, MOD-9012)
MTNKCLLQIALLLCFSTTALSMSYNLLGFLQRSSNFQCQKLLWQLNGRLE

YCLKDRMNFDIPEEIKQLQQFQKEDAALTIYEMLQNIFAIFRQDSSSTGW

NETIVENLLANVYHQINHLKTVLEEKLEKEDFTRGKLMSSLHLKRYYGRI

LHYLKAKEYSHCAWTIVRVEILRNFYFINRLTGYLRNSSSSKAPPPSLPS

PSRLPGPSDTPILPQSSSSKAPPPSLPSPSRLPGPSDTPILPQ.
```

In another embodiment, the polypeptide as described herein comprising an interferon (IFN) peptide- and two CTP units attached to its carboxy terminus is encoded by a nucleic acid molecule set forth in SEQ ID NO: 8. In another embodiment, SEQ ID NO: 8 comprises the following nucleotide acid (NA) sequence:

```
                                  (SEQ ID NO: 8, MOD-9012)
tctagaggacatgaccaacaagtgcctgctgcagatcgccctgctgctgt gcttcagcaccaccgccctgagcatgagctacaacctgctgggcttcctg cagaggtccagcaacttccagtgccagaagctgctgtggcagctgaacgg caggctggaatactgcctgaaggacaggatgaacttcgacatcccagagg aaatcaagcagctgcagcagttccagaaggaggacgccgccctgaccatc tacgagatgctgcagaacatcttcgccatcttcaggcaggacagcagcag caccggctggaacgagaccatcgtggagaacctgctggccaacgtgtacc accagatcaaccacctgaaaaccgtgctggaagagaagctggaaaaggag gacttcaccaggggcaagctgatgagcagcctgcacctgaagaggtacta cggcagaatcctgcactacctgaaggccaaggagtacagccactgcgcct ggaccatcgtgagggtggagatcctgaggaacttctacttcatcaacagg ctgaccggctacctgaggaacagctccagcagcaaggcccctccaccttc cctgcccagtccaagccgactccctgggccctccgacacaccaatcctgc cacagagcagctcctctaaggcccctcctccatccctgccatccccctcc cggctgcctggcccctctgacacccctatcctgcctcagtgatgaaggtc tggatccgcggccgc.
```

In another embodiment, the polypeptide as described herein comprises an interferon (IFN) peptide, a single CTP unit attached to the IFN's amino terminus, and two CTP units attached to the IFN's carboxy terminus. In another embodiment, the polypeptide as described herein comprises an interferon (IFN) peptide, a single CTP unit attached to the IFN's amino terminus and two CTP units attached in tandem to the IFN's carboxy terminus. In another embodiment, the polypeptide as described herein comprises (from amino to carboxy termini): CTP (x1)-interferon (IFN) peptide-CTP (x2) comprising an amino acid sequence set forth in SEQ ID NO: 9. In another embodiment, SEQ ID NO: 9 comprises the following amino acid (AA) sequence:

```
                           (SEQ ID NO: 9, MOD-9013)
MTNKCLLQIALLLCFSTFFALSSSSSKAPPPSLPSPSRLPGPSDTPILPQ

MSYNLLGFLQRSSNEQCQKLLWQLNGRLEYCLKDRMNFDIPEEIKQLQQF

QKEDAALTIYEMLQNIFAIFRQDSSSTGWNETIVENLLANVYHQNHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQSSSSKAP

PPSLPSPSRLPGPSDTPILPQ.
```

In another embodiment, the polypeptide as described herein comprising an interferon (IFN) peptide, a single CTP unit attached to the IFN's amino terminus and two CTP units attached to the IFN's carboxy terminus is encoded by a nucleic acid molecule set forth in SEQ ID NO: 10. In another embodiment, SEQ ID NO: 10 comprises the following nucleotide acid (NA) sequence:

```
                                  (SEQ ID NO: 10, MOD-9013)
tctagaggacatgaccaacaagtgcctgctgcagatcgccctgctgctgt gcttcagcaccaccgccctgagcagcagcagctccaaggccccacccccc agcctgcccagccccagcagactgccaggccccagcgacaccccatcct gccccagatgagctacaacctgctgggcttcctgcagaggtccagcaact tccagtgccagaagctgctgtggcagctgaacggcaggctggaatactgc ctgaaggacaggatgaacttcgacatcccagaggaaatcaagcagctgca gcagttccagaaggaggacgccgccctgaccatctacgagatgctgcaga acatcttcgccatcttcaggcaggacagcagcagcaccggctggaacgag accatcgtggagaacctgctggccaacgtgtaccaccagatcaaccacct gaaaaccgtgctggaagagaagctggaaaaggaggacttcaccaggggca agctgatgagcagcctgcacctgaagaggtactacggcagaatcctgcac tacctgaaggccaaggagtacagccactgcgcctggaccatcgtgagggt ggagatcctgaggaacttctacttcatcaacaggctgaccggctacctga ggaacagctccagcagcaaggcccctccaccttccctgcccagtccaagc cgactccctgggccctccgacacaccaatcctgccacagagcagctcctc taaggcccctcctccatccctgccatccccctcccggctgcctggcccct ctgacacccctatcctgcctcagtgatgaaggtctggatccgcggccgc.
```

In another embodiment, the polypeptide as described herein comprises an interferon (IFN) peptide, a single CTP attached to the IFN's amino terminus, and a single CTP located within an IFN coding sequence. In another embodiment, the polypeptide as described herein comprises (from amino to carboxy termini): CTP (x1)-interferon (IFN) peptide (fragment 1)-CTP-interferon (IFN) peptide (fragment 2)

comprising an amino acid sequence set forth in SEQ ID NO: 11. In another embodiment, SEQ ID NO: 11 comprises the following amino acid (AA) sequence:

(SEQ ID NO: 11, MOD-9014)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

KEDAALTIYEMLQNIFAIFRQDSSSTGWNETIVENLLANVYHQINHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQMSYNLLG

FLQRSSNFQCQKLLWQLNGRLEYCLKDRMNFDIPEEIKQLQQFQKEDAAL

TIYEMLQNIFAIFRQDSSSTGWNETIVENLLANVYHQINHLKTVLEEKLE

KEDFTRGKLMSSLHLKRYYGRILHYLKAKEYSHCAWTIVRVEILRNFYFI

NRLTGYLRN.

In another embodiment, the polypeptide as described herein comprising an interferon (IFN) peptide, a single CTP unit attached to the IFN's amino terminus, and a single CTP unit located within the IFN coding sequence is encoded by a nucleic acid molecule set forth in SEQ ID NO: 12. In another embodiment, SEQ ID NO: 12 comprises the following nucleotide acid (NA) sequence:

(SEQ ID NO: 12, MOD-9014)
tctagaggacatgaccaacaagtgcctgctgcagatcgccctgctgctgt gcttcagcaccaccgccctgagcagcagcagctccaaggcccacccccc agcctgcccagccccagcaggctgccaggccccagcgacaccccatcct gccccagatgagctacaacctgctgggcttcctgcagaggtccagcaact tccagtgccagaaactgctgtggcagctgaacggcaggctggaatactgc ctgaaggaccggatgaacttcgacatccccgaagagatcaagcagctgca gcagttccagaaagaggacgccgccctgaccatctacgagatgctgcaga acatcttcgccatcttcaggcaggacagcagcagcaccggctggaacgag accatcgtggagaacctgctggccaacgtgtaccaccagatcaaccacct gaaaaccgtgctggaagagaagctggaaaaagaggacttcaccaggggca agctgatgagcagcctgcacctgaagaggtactacggcagaatcctgcac tacctgaaggccaaagagtacagccactgcgcctggaccatcgtgagggt ggagatcctgcggaacttctacttcatcaacaggctgaccggctacctga ggaacagctccagcagcaaggcccctccaccctccctgccctccccaagc agactgcccggaccctccgacacaccaattctgccacagatgtcctacaa tctgctcggatttctgcagcgctcctccaactttcagtgtcagaagctcc tctggcagctcaatggccgcctggaatattgtctgaaagacagaatgaat tttgacatcccagaggaaattaaacagctccagcagtttcagaaagaaga tgctgctctcacaatctatgaaatgctccagaatatctttgcaatctttc gccaggacagctcctccaccgggtggaatgagacaattgtcgagaatctg ctcgccaatgtctatcatcagatcaatcacctcaagacagtcctcgaaga aaaactcgaaaagaagatttcacacgcggcaaactgatgtcctccctgc atctgaagcgctactatgggcgcatcctgcattatctgaaagctaaagaa tactcccactgtgcttggacaattgtgcgcgtcgagatcctgagaaactt ttatttcattaaccgcctgacaggatacctgcgcaactgatgaaggtctg gatgcggccgc.

In another embodiment, the polypeptide as described herein comprises an interferon (IFN) peptide and a single CTP unit attached to its amino terminus. In another embodiment, the polypeptide as described herein comprises an interferon (IFN) peptide-CTP comprising an amino acid sequence set forth in SEQ ID NO: 13. In another embodiment, SEQ ID NO: 13 comprises the following amino acid (AA) sequence:

(SEQ ID NO: 13, MOD-9015)
MTNKCLLQIALLLCFSTTALSSSSSKAPPPSLPSPSRLPGPSDTPILPQM

SYNLLGFLQRSSNFQCQKLLWQLNGRLEYCLKDRMNFDIPEEIKQLQQFQ

DEDAALTIYEMLQNIFAIFRQDSSSTGWNETIVENLLANVYHQINHLDTV

LEEKLEKEDFTRGKLMSSLHLKRYYGRILHYLKAKEYSHCAWTIVRVEIL

RNFYFINRLTGYLRN*.

In another embodiment, the polypeptide as described herein comprising an interferon (IFN) peptide- and a single CTP attached to its amino terminus is encoded by a nucleic acid molecule set forth in SEQ ID NO: 14. In another embodiment, SEQ ID NO: 14 comprises the following nucleotide acid (NA) sequence:

(SEQ ID NO: 14, MOD-9015)
tctagaggacatgaccaacaagtgcctgctgcagatcgccctgctgctgt gcttcagcaccaccgccctgagcagcagcagctccaaggcccacccccc agcctgcccagccccagcaggctgccaggccccagcgacaccccatcct gccccagatgagctacaacctgctgggcttcctgcagaggtccagcaact tccagtgccagaaactgctgtggcagctgaacggcaggctggaatactgc ctgaaggaccggatgaacttcgacatccccgaagagatcaagcagctgca gcagttccagaaagaggacgccgccctgaccatctacgagatgctgcaga acatcttcgccatcttcaggcaggacagcagcagcaccggctggaacgag accatcgtggagaacctgctggccaacgtgtaccaccagatcaaccacct gaaaaccgtgctggaagagaagctggaaaaagaggacttcaccaggggca agctgatgagcagcctgcacctgaagaggtactacggcagaatcctgcac tacctgaaggccaaagagtacagccactgcgcctggaccatcgtgagggt ggagatcctgcggaacttctacttcatcaacaggctgaccggctacctga ggaactgatgagtccgcggccgc.

In another embodiment, the polypeptide as described herein comprises an interferon (IFN) peptide, a single CTP unit attached to its amino terminus, and a single CTP unit attached to its carboxy terminus. In another embodiment, the polypeptide as described herein comprises an interferon (IFN) peptide-CTP comprising an amino acid sequence set forth in SEQ ID NO: 15. In another embodiment, SEQ ID NO: 15 comprises the following amino acid (AA) sequence:

```
                                    (SEQ ID NO: 15, MOD-9016)
MTNKCLLQLALLLCFSTFALSSSSSKAPPPSLPSPSRLPGPSDTPILPQM

SYNLLGFLQRSSNEQCQKLLWQLNGRLEYCLKDRMNFDIPEEIKQLQQFQ

KEDAALTIYEMLQNIFAIFRQDSSSTGWNETIVENLLANVYHQLNHLKTV

LEEKLEKEDFTRGKLMSSLHLKRYYGRILHYLKAKEYSHCAWTIVRVEIL

RNFYFINRLTGYLRNSSSSKAPPPSLPSPSRLPGPSDTPILPQ*.
```

In another embodiment, the polypeptide as described herein comprising an interferon (IFN) peptide, a single CTP unit attached to its amino terminus, and a single CTP unit attached to its carboxy terminus is encoded by a nucleic acid molecule set forth in SEQ ID NO: 16. In another embodiment, SEQ ID NO: 16 comprises the following nucleotide acid (NA) sequence:

```
                                    (SEQ ID NO: 16, MOD-9016)
tctagaggacatgaccaacaagtgcctgctgcagatcgccctgctgctgt gcttcagcaccaccgccctgagcagcagcagctccaaggccccaccccc agcctgcccagcccagcagactgccaggccccagcgacaccccatcct gccccagatgagctacaacctgctgggcttcctgcagaggtccagcaact tccagtgccagaagctgctgtggcagctgaacggcaggctggaatactgc ctgaaggacaggatgaacttcgacatcccagaggaaatcaagcagctgca gcagttccagaaggaggacgccgccctgaccatctacgagatgctgcaga acatcttcgccatcttcaggcaggacagcagcagcaccggctggaacgag accatcgtggagaacctgctggccaacgtgtaccaccagatcaaccacct gaaaaccgtgctggaagagaagctggaaaaggaggacttcaccaggggca agctgatgagcagcctgcacctgaagaggtactacggcagaatcctgcac tacctgaaggccaaggagtacagccactgcgcctggaccatcgtgagggt ggagatcctgaggaacttctacttcatcaacaggctgaccggctacctga ggaacagctccagcagcaaggcccctccaccttccctgcccagtccaagc cgactccctgggccctccgatacaccaattctgccacagtgatgaaggtc tggatgcggccgc.
```

In another embodiment, an interferon β peptide comprises SEQ ID NO: 21 comprising the following amino acid (AA) sequence:

```
                                    (SEQ ID NO: 21)
MSYNLLGFLQRSSNFQSQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYFRILHYLKAKEYSHCAWTIVRVEI

LRNFYFINRLTGYLRN.
```

In another embodiment, a polypeptide as described herein comprises IFN protein connected via a peptide bond to at least one CTP unit. In another embodiment, a polypeptide as described herein comprises IFN protein connected via a peptide bond to at least one CTP unit which is connected to an additional CTP unit via a peptide bond. In another embodiment, a polypeptide as described herein comprising IFN protein and/or fragments thereof and CTP units and/or fragments thereof that are interconnected via a peptide bond. In another embodiment, one nucleic acid molecule encodes a polypeptide as described herein comprising IFN protein and/or fragments thereof and CTP units and/or fragments thereof.

In some embodiments, a CTP sequences at both the amino terminal end of a polypeptide and at the carboxy terminal end of the polypeptide provide enhanced protection against degradation of a protein. In another embodiment, at least one CTP sequence at the amino terminal end of a IFN and two CTP units in the carboxy terminal end of IFN provide enhanced protection against degradation of an IFN protein. In another embodiment, at least one CTP sequence at the amino terminal end of an IFN and at least two CTP units in the carboxy terminal end of IFN provide enhanced protection against degradation of an IFN protein. In another embodiment, a single CTP sequence at the amino terminal end of a IFN and at least two CTP units in the carboxy terminal end of IFN provide enhanced protection against degradation of an IFN protein. In some embodiments, CTP sequences at both the amino terminal end of a polypeptide and at the carboxy terminal end of the polypeptide provide extended half-life of the attached protein. In another embodiment, at least a single CTP sequence at the amino terminal end of a polypeptide and at least two CTP sequences at the carboxy terminal end of the polypeptide provide extended half-life of the attached interferon protein. In another embodiment, a single CTP sequence at the amino terminal end of a polypeptide and two CTP sequences at the carboxy terminal end of the polypeptide provide extended half-life of the attached interferon protein. In another embodiment, a single CTP sequence at the amino terminal end of a polypeptide and two CTP sequences in tandem at the carboxy terminal end of the polypeptide provide extended half-life of the attached interferon protein.

In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced protection against degradation of a protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide extended half-life of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced activity of the attached protein.

In some embodiments, a CTP sequence at the amino terminal end of a polypeptide, a CTP sequence at the carboxy terminal end of the polypeptide, and at least one additional CTP sequence attached in tandem to the CTP sequence at the carboxy or amino terminus provide enhanced protection against degradation of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide extended half-life of the attached protein. In some embodiments, a CTP sequence at the amino terminal end of a polypeptide, a CTP sequence at the carboxy terminal end of the polypeptide, and at least one additional CTP sequence attached in tandem to the CTP sequence at the carboxy terminus provide enhanced activity of the attached protein. In another embodiment, a CTP sequence at the amino terminal end of a polypeptide, two CTP sequences at the carboxy terminal end of the polypeptide, and at least one additional CTP sequence attached in tandem to the CTP sequence at the amino or carboxy terminus provide enhanced activity of the attached protein.

In another embodiment, the carboxy terminal peptide (CTP) peptide of the present invention comprises the amino acid sequence from amino acid 112 to position 145 of human chorionic gonadotrophin, as set forth in SEQ ID NO: 17. In another embodiment, the CTP sequence of the present invention comprises the amino acid sequence from amino acid 118 to position 145 of human chorionic gonadotropin, as set forth in SEQ ID NO: 18. In another embodiment, the CTP sequence also commences from any position between positions 112-118 and terminates at position 145 of human chorionic gonadotrophin. In some embodiments, the CTP sequence peptide is 28, 29, 30, 31, 32, 33 or 34 amino acids long and commences at position 112, 113, 114, 115, 116, 117 or 118 of the CTP amino acid sequence.

In another embodiment, the CTP peptide is a variant of chorionic gonadotrophin CTP which differs from the native CTP by 1-5 conservative amino acid substitutions as described in U.S. Pat. No. 5,712,122. In another embodiment, the CTP peptide is a variant of chorionic gonadotrophin CTP which differs from the native CTP by 1 conservative amino acid substitution. In another embodiment, the CTP peptide is a variant of chorionic gonadotrophin CTP which differs from the native CTP by 2 conservative amino acid substitutions. In another embodiment, the CTP peptide is a variant of chorionic gonadotrophin CTP which differs from the native CTP by 3 conservative amino acid substitutions. In another embodiment, the CTP peptide is a variant of chorionic gonadotrophin CTP which differs from the native CTP by 4 conservative amino acid substitutions. In another embodiment, the CTP peptide is a variant of chorionic gonadotrophin CTP which differs from the native CTP by 5 conservative amino acid substitutions. In another embodiment, the CTP peptide amino acid sequence of the present invention is at least 70% homologous to the native CTP amino acid sequence or a peptide thereof. In another embodiment, the CTP peptide amino acid sequence of the present invention is at least 80% homologous to the native CTP amino acid sequence or a peptide thereof. In another embodiment, the CTP peptide amino acid sequence of the present invention is at least 90% homologous to the native CTP amino acid sequence or a peptide thereof. In another embodiment, the CTP peptide amino acid sequence of the present invention is at least 95% homologous to the native CTP amino acid sequence or a peptide thereof.

In one embodiment, the CTP peptide DNA sequence of the present invention is at least 70% homologous to the native CTP DNA sequence or a peptide thereof. In one embodiment, the CTP peptide DNA sequence of the present invention is at least 80% homologous to the native CTP DNA sequence or a peptide thereof. In one embodiment, the CTP peptide DNA sequence of the present invention is at least 90% homologous to the native CTP DNA sequence or a peptide thereof. In one embodiment, the CTP peptide DNA sequence of the present invention is at least 95% homologous to the native CTP DNA sequence or a peptide thereof.

In one embodiment, at least one of the chorionic gonadotrophin CTP amino acid sequences is truncated. In another embodiment, both of the chorionic gonadotrophin CTP amino acid sequences are truncated. In another embodiment, 2 of the chorionic gonadotrophin CTP amino acid sequences are truncated. In another embodiment, 2 or more of the chorionic gonadotrophin CTP amino acid sequences are truncated. In another embodiment, all of the chorionic gonadotrophin CTP amino acid sequences are truncated. In one embodiment, the truncated CTP comprises the first 10 amino acids of SEQ ID NO: 22. In another embodiment, SEQ ID NO: 22 comprises the following amino acid (AA) sequence: SSSSKAPPSLP.

In one embodiment, the truncated CTP comprises the first 9 amino acids of SEQ ID NO: 22. In one embodiment, the truncated CTP comprises the first 8 amino acids of SEQ ID NO: 22. In one embodiment, the truncated CTP comprises the first 7 amino acids of SEQ ID NO: 22. In one embodiment, the truncated CTP comprises the first 6 amino acids of SEQ ID NO: 22. In one embodiment, the truncated CTP comprises the first 5 amino acids of SEQ ID NO: 22. In one embodiment, the truncated CTP comprises the first 4 amino acids of SEQ ID NO: 22.

In one embodiment, at least one of the chorionic gonadotrophin CTP amino acid sequences is glycosylated. In another embodiment, both of the chorionic gonadotrophin CTP amino acid sequences are glycosylated. In another embodiment, 2 of the chorionic gonadotrophin CTP amino acid sequences are glycosylated. In another embodiment, 2 or more of the chorionic gonadotrophin CTP amino acid sequences are glycosylated. In another embodiment, all of the chorionic gonadotrophin CTP amino acid sequences are glycosylated. In one embodiment, the CTP sequence of the present invention comprises at least one glycosylation site. In one embodiment, the CTP sequence of the present invention comprises 2 glycosylation sites. In one embodiment, the CTP sequence of the present invention comprises 3 glycosylation sites. In one embodiment, the CTP sequence of the present invention comprises 4 glycosylation sites.

In one embodiment, IFN sequence of the present invention also refers to homologues. In another embodiment, IFN sequence of the present invention also refers to homologues of IFN sequences as described hereinabove. In another embodiment, the IFN amino acid sequence of the present invention is at least 50% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 60% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 70% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 80% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 90% homologous to an IFN sequence set forth in GenBank Accession No. NP_002167.1 as determined using BlastP software of the National Center of Biotechnology Information (NCBI) using default parameters). In another embodiment, the IFN amino acid sequence of the present invention is at least 95% homologous to an IFN sequence set forth in GenBank Accession No. NP_002167.1 as determined using BlastP software of the National Center of Biotechnology Information (NCBI) using default parameters). In another embodiment, homology according to the present invention also encompasses deletions, insertions, or substitution variants, including an amino acid substitution, thereof and biologically active polypeptide fragments thereof. In another embodiment, the cysteine interferon β peptide comprises SEQ ID NO: 21 comprising the following amino acid (AA) sequence:

(SEQ ID NO: 21).
MSYNLLGFLQRSSNFQSQKLLWQLNGRLEYCLKDRMNFDIPEEIKQLQQF

QKEDAALTIYEMLQNIFAIFRQDSSSTGWNETIVENLLANVYHQINHLKT

VLEEKLEKEDFTRGKLMSSLHLKRYYFRILHYLKAKEYSHCAWTIVRVEI

LRNFYFINRLTGYLRN.

In another embodiment, the term "interferon" refers to the mammalian interferon polypeptide (e.g., Type I or Type II interferon) which exhibits an interferon activity, e.g. antiviral or antiproliferative activity. In another embodiment, GenBank accession numbers. of non-limiting examples of interferons are listed in Table 1 below. An interferon of the present invention also refers in one embodiment, to homologs (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to interferon sequences listed in Table 1 as determined using BlastP software of the National Center of Biotechnology Information (NCBI) using default parameters). In another embodiment, homolog may also refer to a deletion, insertion, or substitution variant, including an amino acid substitution, thereof and biologically active polypeptide fragments thereof. In another embodiment, a variety of suitable interferon polypeptides are known to those of ordinary skill in the art. In another embodiment, interferon is a Type I or Type II interferon, including those commonly designated as alpha-interferon, beta-interferon, gamma-interferon, and omega-interferon. In another embodiment, interferon is a subspecie such as of a type I or Type II interferon (e.g. IFN-α2a IFN-α2b, IFN-β$_1$a and IFN-β$_1$b).

Table 1 below lists examples of interferons with their respective NCBI sequence numbers.

TABLE 1

| Interferon name | NCBI sequence number |
|---|---|
| interferon, α1 | NP_076918.1 |
| interferon, α10 | NP_002162.1 |
| interferon, α13 | NP_008831.2 |
| interferon, α14 | NP_002163.1 |
| interferon, α16 | NP_002164.1 |
| interferon, α17 | NP_067091.1 |
| interferon, α2 | NP_000596.2 |
| interferon, α21 | NP_002166.1 |
| interferon, α4 | NP_066546.1 |
| interferon, α5 | NP_002160.1 |
| interferon, α6 | NP_066282.1 |
| interferon, α7 | NP_066401.2 |
| interferon, α8 | NP_002161.2 |
| interferon, β1 | NP_002167.1 |
| interferon, ε1 | NP_795372.1 |
| interferon, γ | NP_000610.2 |
| interferon, ε | NP_064509.1 |
| interferon, Ω1 | NP_002168.1 |

In another embodiment, a method of treating or reducing a disease treatable or reducible by an interferon or a pharmaceutical formulation comprising the same, in a subject, comprises the step of administering to a subject a therapeutically effective amount of the polypeptide comprising IFN protein and CTP units as described herein, thereby treating or reducing a disease treatable or reducible by an interferon in a subject.

In another embodiment, a disease treatable or reducible by an interferon is hepatitis C infection, cancer, bacterial infection, viral infection, injury, multiple sclerosis, hairy cell leukemia, malignant melanoma, Kaposi's sarcoma, bladder cancer, chronic myelocytic leukemia, kidney cancer, carcinoid tumors, non-Hodgkin's lymphoma, ovarian cancer, skin chronic hepatitis C(CHC), condylomata acuminata (CA), chronic hepatitis B, follicular non-Hodgkin's lymphoma, chronic granulomatous disease, *Mycobacterium avium* complex (MAC), pulmonary fibrosis osteoarthritis, and osteoporosis.

In another embodiment, polypeptides of the present invention comprising IFN α-2a as well as pharmaceutical compositions comprising the same are indicated for hairy cell leukemia (HCL), acquired immune deficiency syndrome (AIDS)-related Kaposi's sarcoma (KS), chronic-phase Philadelphia (Ph) chromosome-positive chronic myelogenous leukemia (CML) and chronic hepatitis C(CHC). IFN α-2a dosage varies depending on the indication. In another embodiment, the effectiveness of IFN α-2a as an antineoplastic, immunomodulator and antiviral agent has been established.

In another embodiment, polypeptides of the present invention comprising IFN α-2b as well as pharmaceutical compositions comprising the same are indicated for HCL, AIDS-related Kaposi's sarcoma and CHC. It is also indicated for condylomata acuminata (CA), chronic hepatitis B, malignant melanoma and follicular non-Hodgkin's lymphoma. IFN α-2b dosage varies depending on its indication of usage.

In another embodiment, a subject is a human subject. In another embodiment, a subject is a pet. In another embodiment, a subject is a mammal. In another embodiment, a subject is a farm animal. In another embodiment, a subject is a monkey. In another embodiment, a subject is a horse. In another embodiment, a subject is a cow. In another embodiment, a subject is a mouse. In another embodiment, a subject is a rat.

In another embodiment, a polypeptide comprising an IFN protein, at least a single CTP attached to its carboxy terminus, and at least a single CTP attached to its amino terminus is used to trigger an immune response. In another embodiment, a polypeptide comprising an IFN protein, a single CTP attached to its amino terminus, and at least two CTP units attached to its carboxy terminus is used to trigger an immune response. In another embodiment, a polypeptide comprising an IFN protein, a single CTP attached to its amino terminus, and two CTP units attached to its carboxy terminus is used to trigger an immune response. In another embodiment, a polypeptide comprising an IFN protein and CTP units is formulated in a pharmaceutical composition that is administered to a subject in need of triggering an immune response.

In another embodiment, a polypeptide comprising an IFN protein and CTP units as described herein is used to trigger an immune response against a viral infection. In another embodiment, a polypeptide comprising an IFN protein and CTP units is formulated in a pharmaceutical composition that is administered to a subject in need of triggering an immune response against a viral infection.

In another embodiment, a polypeptide comprising an IFN β and CTP units as described herein is used to trigger an immune response via the enhancement of activity of lymphocyte cells. In another embodiment, a polypeptide comprising an IFN β and CTP units is formulated in a pharmaceutical composition that is administered to a subject in need of triggering an immune response via the enhancement of activity of lymphocyte cells.

In another embodiment, a polypeptide comprising an IFN α and CTP units as described herein is used as an anti-tumor agent. In another embodiment, a polypeptide comprising an IFN α and CTP units is formulated in a pharmaceutical composition that is administered to a patient afflicted with cancer.

In another embodiment, a polypeptide comprising an IFN protein and CTP units as described herein is used equivalently to a regular or a recombinant interferon as known to one of average skill in the art. In another embodiment, a polypeptide comprising an IFN protein and CTP units is formulated equivalently to a regular or a recombinant interferon as known to one of average skill in the art.

In another embodiment, a polypeptide comprising an IFN protein and CTP units as described herein enhances the activity of T-cells, while simultaneously reducing the production cytokines that operate in the inflammatory response to infection and injury. In another embodiment, a polypeptide comprising an IFN protein and CTP units is formulated in a pharmaceutical composition that is administered to a patient in need of T-cells activity enhancement. In another embodiment, a polypeptide comprising an IFN protein and CTP units is formulated in a pharmaceutical composition that is administered to a patient afflicted with multiple sclerosis. In another embodiment, a polypeptide comprising an IFN protein and CTP units is formulated in a pharmaceutical composition that is administered to a patient afflicted with hepatitis C infection.

In another embodiment, a polypeptide comprising an IFN protein and CTP units is formulated in an intranasal dosage form. In another embodiment, a polypeptide comprising an IFN protein and CTP units is formulated in an injectable dosage form. In another embodiment, a polypeptide comprising an IFN protein and CTP units is administered to a subject in a dose ranging from 0.0001 mg to 0.6 mg. In another embodiment, a polypeptide comprising an IFN protein and CTP units is administered to a subject in a dose ranging from 0.001 mg to 0.005 mg. In another embodiment, a polypeptide comprising an IFN protein and CTP units is administered to a subject in a dose ranging from 0.005 mg to 0.01 mg. In another embodiment, a polypeptide comprising an IFN protein and CTP units is administered to a subject in a dose ranging from 0.01 mg to 0.3 mg. In another embodiment, a polypeptide comprising an IFN protein and CTP units is administered to a subject in a dose in a dose ranging from 0.2 mg to 0.6 mg.

In another embodiment, a polypeptide comprising an IFN protein and CTP units is administered to a subject in a dose ranging from 1-100 micrograms. In another embodiment, a polypeptide comprising an IFN protein and CTP units is administered to a subject in a dose ranging from 10-80 micrograms. In another embodiment, a polypeptide comprising an IFN protein and CTP units is administered to a subject in a dose ranging from 20-60 micrograms. In another embodiment, a polypeptide comprising an IFN protein and CTP units is administered to a subject in a dose ranging from 10-50 micrograms. In another embodiment, a polypeptide comprising an IFN protein and CTP units is administered to a subject in a dose ranging from 40-80 micrograms. In another embodiment, a polypeptide comprising an IFN protein and CTP units is administered to a subject in a dose ranging from 10-30 micrograms. In another embodiment, a polypeptide comprising an IFN protein and CTP units is administered to a subject in a dose ranging from 30-60 micrograms.

In another embodiment, a polypeptide comprising an IFN protein and CTP units is administered to a subject in a dose ranging from 0.2 mg to 2 mg. In another embodiment, a polypeptide comprising an IFN protein and CTP units is administered to a subject in a dose ranging from 2 mg to 6 mg. In another embodiment, a polypeptide comprising an IFN protein and CTP units is administered to a subject in a dose ranging from 4 mg to 10 mg. In another embodiment, a polypeptide comprising an IFN protein and CTP units is administered to a subject in a dose ranging from 5 mg and 15 mg.

In another embodiment, a polypeptide comprising an IFN protein and CTP units is injected into the muscle (intramuscular injection). In another embodiment, a polypeptide comprising an IFN protein and CTP units is injected below the skin (subcutaneous injection).

In another embodiment, a polypeptide comprising an IFN protein and CTP units is administered to a subject once a day. In another embodiment, a polypeptide comprising an IFN protein and CTP units is administered to a subject once every two days. In another embodiment, a polypeptide comprising an IFN protein and CTP units is administered to a subject once every three days. In another embodiment, a polypeptide comprising an IFN protein and CTP units is administered to a subject once every four days. In another embodiment, a polypeptide comprising an IFN protein and CTP units is administered to a subject once every five days. In another embodiment, a polypeptide comprising an IFN protein and CTP units is administered to a subject once every six days. In another embodiment, a polypeptide comprising an IFN protein and CTP units is administered to a subject once every week. In another embodiment, a polypeptide comprising an IFN protein and CTP units is administered to a subject once every 7-14 days. In another embodiment, a polypeptide comprising an IFN protein and CTP units is administered to a subject once every 10-20 days. In another embodiment, a polypeptide comprising an IFN protein and CTP units is administered to a subject once every 5-15 days. In another embodiment, a polypeptide comprising an IFN protein and CTP units is administered to a subject once every 15-30 days.

In another embodiment, the methods of the present invention provide an interferon beta 1 peptide having additionally at least one CTP amino acid peptide on the N-terminus and at least one CTP amino acid peptide on the C-terminus for treating or inhibiting multiple sclerosis. In another embodiment, the methods of the present invention provide an interferon beta 1 peptide having additionally one CTP amino acid peptide on the N-terminus and two CTP amino acid peptides on the C-terminus for treating or inhibiting multiple sclerosis. In another embodiment, the methods of the present invention provide an interferon beta 1 peptide set forth in SEQ ID NOs: 5, 7, 9, 11, 13, or 15 for treating diseases such as but not limited to multiple sclerosis, cancer, or viral infections. In another embodiment, the methods of the present invention provide an interferon beta 1 peptide set forth in SEQ ID NOs: 5, 7, 9, 11, 13, or 15 for treating diseases such as but not limited to multiple sclerosis, cancer, or viral infections. In another embodiment, the methods of the present invention provide an interferon beta 1 peptide set forth in SEQ ID NO: 9 for treating diseases such as but not limited to multiple sclerosis, cancer, or viral infections. In another embodiment, the methods of the present invention provide an interferon beta 1 peptide set forth in SEQ ID NO: 11 for treating diseases such as but not limited to multiple sclerosis, cancer, or viral infections. In another embodiment, the methods of the present invention provide an interferon beta 1 peptide set forth in SEQ ID NO: 13 for treating diseases such as but not limited to multiple sclerosis, cancer, or viral infections. In another embodiment, the methods of the present invention provide an interferon beta 1 peptide set forth in SEQ ID NO:

15 for treating diseases such as but not limited to multiple sclerosis, cancer, or viral infections.

In some embodiments, modifications include, but are not limited to N terminus modification, C terminus modification, polypeptide bond modification, including, but not limited to, CH2-NH, CH2-S, CH2-S=O, O=C—NH, CH2-O, CH2-CH2, S=C—NH, CH=CH or CF=CH, backbone modifications, and residue modification. Methods for preparing peptidomimetic compounds are well known in the art and are specified, for example, in Quantitative Drug Design, C. A. Ramsden Gd., Chapter 17.2, F. Choplin Pergamon Press (1992), which is incorporated by reference as if fully set forth herein. Further details in this respect are provided hereinunder.

In some embodiments, polypeptide bonds (—CO—NH—) within the polypeptide are substituted. In some embodiments, the polypeptide bonds are substituted by N-methylated bonds (—N(CH3)-CO—). In some embodiments, the polypeptide bonds are substituted by ester bonds (—C(R)H—C—O—O—C(R)—N—). In some embodiments, the polypeptide bonds are substituted by ketomethylen bonds (—CO—CH2-). In some embodiments, the polypeptide bonds are substituted by α-aza bonds (—NH—N(R)—CO—), wherein R is any alkyl, e.g., methyl, carba bonds (—CH2-NH—). In some embodiments, the polypeptide bonds are substituted by hydroxyethylene bonds (—CH(OH)—CH2-). In some embodiments, the polypeptide bonds are substituted by thioamide bonds (—CS—NH—). In some embodiments, the polypeptide bonds are substituted by olefinic double bonds (—CH=CH—). In some embodiments, the polypeptide bonds are substituted by retro amide bonds (—NH—CO—). In some embodiments, the polypeptide bonds are substituted by polypeptide derivatives (—N(R)—CH2-CO—), wherein R is the "normal" side chain, naturally presented on the carbon atom. In some embodiments, these modifications occur at any of the bonds along the polypeptide chain and even at several (2-3 bonds) at the same time.

In some embodiments, natural aromatic amino acids of the polypeptide such as Trp, Tyr and Phe, are substituted for synthetic non-natural acid such as Phenylglycine, TIC, naphthylelanine (Nol), ring-methylated derivatives of Phe, halogenated derivatives of Phe or o-methyl-Tyr. In some embodiments, the polypeptides of the present invention include one or more modified amino acid or one or more non-amino acid monomers (e.g. fatty acid, complex carbohydrates etc).

In one embodiment, "amino acid" or "amino acid" is understood to include the 20 naturally occurring amino acid; those amino acid often modified post-translationally in vivo, including, for example, hydroxyproline, phosphoserine and phosphothreonine; and other unusual amino acid including, but not limited to, 2-aminoadipic acid, hydroxylysine, isodesmosine, nor-valine, nor-leucine and ornithine. In one embodiment, "amino acid" includes both D- and L-amino acid.

In some embodiments, the polypeptides of the present invention are utilized in therapeutics which requires the polypeptides to be in a soluble form. In some embodiments, the polypeptides of the present invention include one or more non-natural or natural polar amino acid, including but not limited to serine and threonine which are capable of increasing polypeptide solubility due to their hydroxyl-containing side chain.

In some embodiments, the interferon of present invention is biochemically synthesized such as by using standard solid phase techniques. In some embodiments, these biochemical methods include exclusive solid phase synthesis, partial solid phase synthesis, fragment condensation, or classical solution synthesis. In some embodiments, these methods are used when the polypeptide is relatively short (about 5-15 kDa) and/or when it cannot be produced by recombinant techniques (i.e., not encoded by a nucleic acid sequence) and therefore involves different chemistry.

In some embodiments, solid phase polypeptide synthesis procedures are well known to one skilled in the art and further described by John Morrow Stewart and Janis Dillaha Young, Solid Phase Polypeptide Syntheses (2nd Ed., Pierce Chemical Company, 1984). In some embodiments, synthetic polypeptides are purified by preparative high performance liquid chromatography [Creighton T. (1983) Proteins, structures and molecular principles. WH Freeman and Co. N.Y.] and the composition of which can be confirmed via amino acid sequencing by methods known to one skilled in the art.

In some embodiments, recombinant protein techniques are used to generate the polypeptides of the present invention. In some embodiments, recombinant protein techniques are used for generation of relatively long polypeptides (e.g., longer than 18-25 amino acid). In some embodiments, recombinant protein techniques are used for the generation of large amounts of the polypeptide of the present invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al. (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

In another embodiment, an interferon of the present invention is synthesized using a polynucleotide encoding a polypeptide of the present invention. In some embodiments, the polynucleotide encoding an interferon of the present invention is ligated into an expression vector, comprising a transcriptional control of a cis-regulatory sequence (e.g., promoter sequence). In some embodiments, the cis-regulatory sequence is suitable for directing constitutive expression of the interferon of the present invention. In some embodiments, the cis-regulatory sequence is suitable for directing tissue specific expression of the interferon of the present invention. In some embodiments, the cis-regulatory sequence is suitable for directing inducible expression of the interferon of the present invention.

In some embodiments, polynucleotides which express the polypeptides of the present invention are as set forth in SEQ ID NOs: 6, 8, 10, 12, 14, and 16.

In some embodiment, tissue-specific promoters suitable for use with the present invention include sequences which are functional in specific cell population, example include, but are not limited to promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230: 912-916] or mammary gland-specific promoters such as the milk whey promoter (U.S. Pat. No. 4,873,316 and European Application Publication No. 264,166). Inducible promoters suitable for use with the present invention include for example the tetracycline-inducible promoter (Srour, M. A., et al., 2003. Thromb. Haemost. 90: 398-405).

In one embodiment, the phrase "a polynucleotide" refers to a single or double stranded nucleic acid sequence which be isolated and provided in the form of an RNA sequence, a complementary polynucleotide sequence (cDNA), a genomic polynucleotide sequence and/or a composite polynucleotide sequences (e.g., a combination of the above).

In one embodiment, "complementary polynucleotide sequence" refers to a sequence, which results from reverse transcription of messenger RNA using a reverse transcriptase or any other RNA dependent DNA polymerase. In one embodiment, the sequence can be subsequently amplified in vivo or in vitro using a DNA polymerase.

In one embodiment, "genomic polynucleotide sequence" refers to a sequence derived (isolated) from a chromosome and thus it represents a contiguous portion of a chromosome.

In one embodiment, "composite polynucleotide sequence" refers to a sequence, which is at least partially complementary and at least partially genomic. In one embodiment, a composite sequence can include some exonal sequences required to encode the polypeptide of the present invention, as well as some intronic sequences interposing therebetween. In one embodiment, the intronic sequences can be of any source, including of other genes, and typically will include conserved splicing signal sequences. In one embodiment, intronic sequences include cis acting expression regulatory elements.

In one embodiment, the polynucleotides of the present invention further comprise a signal sequence encoding a signal peptide for the secretion of the polypeptides of the present invention. In some embodiments, signal sequences include, but are not limited to the endogenous signal sequence for IFN-β1 as set forth in SEQ ID NO: 19. In another embodiment, the signal sequence is N-terminal to the CTP sequence that is in turn N-terminal to the polypeptide sequence of interest; e.g. the sequence is (a) signal sequence-(b) CTP-(c) sequence-of-interest-(d) optionally 1 or more additional CTP sequences. In another embodiment, 1 or more CTP sequences is inserted between the signal sequence of a polypeptide sequence of interest and the polypeptide sequence of interest itself, thus interrupting the wild-type sequence of interest. Each possibility represents a separate embodiment of the present invention.

In one embodiment, following expression and secretion, the signal peptides are cleaved from the precursor proteins resulting in the mature proteins.

In some embodiments, polynucleotides of the present invention are prepared using PCR techniques as described in Example 1, or any other method or procedure known to one skilled in the art. In some embodiments, the procedure involves the ligation of two different DNA sequences (See, for example, "Current Protocols in Molecular Biology", eds. Ausubel et al., John Wiley & Sons, 1992).

In one embodiment, polynucleotides of the present invention are inserted into expression vectors (i.e., a nucleic acid construct) to enable expression of the recombinant polypeptide. In one embodiment, the expression vector of the present invention includes additional sequences which render this vector suitable for replication and integration in prokaryotes. In one embodiment, the expression vector of the present invention includes additional sequences which render this vector suitable for replication and integration in eukaryotes. In one embodiment, the expression vector of the present invention includes a shuttle vector which renders this vector suitable for replication and integration in both prokaryotes and eukaryotes. In some embodiments, cloning vectors comprise transcription and translation initiation sequences (e.g., promoters, enhances) and transcription and translation terminators (e.g., polyadenylation signals).

In one embodiment, a variety of prokaryotic or eukaryotic cells can be used as host-expression systems to express the polypeptides of the present invention. In some embodiments, these include, but are not limited to, microorganisms, such as bacteria transformed with a recombinant bacteriophage DNA, plasmid DNA or cosmid DNA expression vector containing the polypeptide coding sequence; yeast transformed with recombinant yeast expression vectors containing the polypeptide coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the polypeptide coding sequence.

In some embodiments, non-bacterial expression systems are used (e.g. mammalian expression systems such as CHO cells) to express the polypeptide of the present invention. In one embodiment, the expression vector used to express polynucleotides of the present invention in mammalian cells is pCI-DHFR vector comprising a CMV promoter and a neomycin resistance gene. Construction of the pCI-dhfr vector is described, according to one embodiment, in Example 1.

In some embodiments, in bacterial systems of the present invention, a number of expression vectors can be advantageously selected depending upon the use intended for the polypeptide expressed. In one embodiment, large quantities of polypeptide are desired. In one embodiment, vectors that direct the expression of high levels of the protein product, possibly as a fusion with a hydrophobic signal sequence, which directs the expressed product into the periplasm of the bacteria or the culture medium where the protein product is readily purified are desired. In one embodiment, certain fusion protein engineered with a specific cleavage site to aid in recovery of the polypeptide. In one embodiment, vectors adaptable to such manipulation include, but are not limited to, the pET series of *E. coli* expression vectors [Studier et al., Methods in Enzymol. 185:60-89 (1990)].

In one embodiment, yeast expression systems are used. In one embodiment, a number of vectors containing constitutive or inducible promoters can be used in yeast as disclosed in U.S. Pat. No. 5,932,447. In another embodiment, vectors which promote integration of foreign DNA sequences into the yeast chromosome are used.

In one embodiment, the expression vector of the present invention can further include additional polynucleotide sequences that allow, for example, the translation of several proteins from a single mRNA such as an internal ribosome entry site (IRES) and sequences for genomic integration of the promoter-chimeric polypeptide.

In some embodiments, mammalian expression vectors include, but are not limited to, pcDNA3, pcDNA3.1 (+/−), pGL3, pZeoSV2(+/−), pSecTag2, pDisplay, pEF/myc/cyto, pCMV/myc/cyto, pCR3.1, pSinRepS, DH26S, DHBB, pNMT1, pNMT41, pNMT81, which are available from Invitrogen, pCI which is available from Promega, pMbac, pPbac, pBK-RSV and pBK-CMV which are available from Stratagene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-IMTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors are useful for in vivo expression of the polypeptides of the present invention since they offer advantages such as lateral infection and targeting specificity. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

In one embodiment, various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, introduction of nucleic acid by viral infection offers several advantages over other methods such as lipofection and electroporation, since higher transfection efficiency can be obtained due to the infectious nature of viruses.

In one embodiment, it will be appreciated that the polypeptides of the present invention can also be expressed from a nucleic acid construct administered to the individual employing any suitable mode of administration, described hereinabove (i.e., in-vivo gene therapy). In one embodiment, the nucleic acid construct is introduced into a suitable cell via an appropriate gene delivery vehicle/method (transfection, transduction, homologous recombination, etc.) and an expression system as needed and then the modified cells are expanded in culture and returned to the individual (i.e., ex-vivo gene therapy).

In one embodiment, in vivo gene therapy using IFN has been attempted in animal models such as rodents.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach [Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

Various methods, in some embodiments, can be used to introduce the expression vector of the present invention into the host cell system. In some embodiments, such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In some embodiments, transformed cells are cultured under effective conditions, which allow for the expression of high amounts of recombinant polypeptide. In some embodiments, effective culture conditions include, but are not limited to, effective media, bioreactor, temperature, pH and oxygen conditions that permit protein production. In one embodiment, an effective medium refers to any medium in which a cell is cultured to produce the recombinant polypeptide of the present invention. In some embodiments, a medium typically includes an aqueous solution having assimilable carbon, nitrogen and phosphate sources, and appropriate salts, minerals, metals and other nutrients, such as vitamins. In some embodiments, cells of the present invention can be cultured in conventional fermentation bioreactors, shake flasks, test tubes, microtiter dishes and petri plates. In some embodiments, culturing is carried out at a temperature, pH and oxygen content appropriate for a recombinant cell. In some embodiments, culturing conditions are within the expertise of one of ordinary skill in the art.

In some embodiments, depending on the vector and host system used for production, resultant polypeptides of the present invention either remain within the recombinant cell, secreted into the fermentation medium, secreted into a space between two cellular membranes, such as the periplasmic space in *E. coli*; or retained on the outer surface of a cell or viral membrane.

In one embodiment, following a predetermined time in culture, recovery of the recombinant polypeptide is effected.

In one embodiment, the phrase "recovering the recombinant polypeptide" used herein refers to collecting the whole fermentation medium containing the polypeptide and need not imply additional steps of separation or purification.

In one embodiment, polypeptides of the present invention are purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

In one embodiment, to facilitate recovery, the expressed coding sequence can be engineered to encode the polypeptide of the present invention and fused cleavable moiety. In one embodiment, a fusion protein can be designed so that the polypeptide can be readily isolated by affinity chromatography; e.g., by immobilization on a column specific for the cleavable moiety. In one embodiment, a cleavage site is engineered between the polypeptide and the cleavable moiety and the polypeptide can be released from the chromatographic column by treatment with an appropriate enzyme or agent that specifically cleaves the fusion protein at this site [e.g., see Booth et al., Immunol. Lett. 19:65-70 (1988); and Gardella et al., J. Biol. Chem. 265:15854-15859 (1990)].

In one embodiment, the polypeptide of the present invention is retrieved in "substantially pure" form.

In one embodiment, the phrase "substantially pure" refers to a purity that allows for the effective use of the protein in the applications described herein.

In one embodiment, the polypeptide of the present invention can also be synthesized using in vitro expression systems. In one embodiment, in vitro synthesis methods are well known in the art and the components of the system are commercially available.

In some embodiments, the recombinant polypeptides are synthesized and purified; their therapeutic efficacy can be assayed either in vivo or in vitro. In one embodiment, the binding activities of the recombinant IFN polypeptides of the present invention can be ascertained using various assays as described in Examples 2-6 and 8-9.

In another embodiment, a polypeptide as described herein comprising IFN as well as pharmaceutical compositions comprising the same are used to treat cancers such as hairy cell leukemia, malignant melanoma, Kaposi's sarcoma, bladder cancer, chronic myelocytic leukemia, kidney cancer, carcinoid tumors, non-Hodgkin's lymphoma, ovarian cancer, and skin cancers.

In another embodiment, polypeptides of the present invention comprising IFN as well as pharmaceutical compositions comprising the same are used to treat a subject afflicted with chronic hepatitis C(CHC), condylomata acuminata (CA), chronic hepatitis B, follicular non-Hodgkin's lymphoma, multiple sclerosis, chronic granulomatous disease, *Mycobacterium avium* complex (MAC), pulmonary fibrosis osteoarthritis, and osteoporosis.

In another embodiment, polypeptides of the present invention comprising IFN α-2a as well as pharmaceutical compositions comprising the same are indicated for hairy cell leukemia (HCL), acquired immune deficiency syndrome (AIDS)-related Kaposi's sarcoma (KS), chronic-phase Philadelphia (Ph) chromosome-positive chronic myelogenous leukemia (CML) and chronic hepatitis C(CHC). IFN α-2a dosage varies depending on the indication. In another embodiment, the effectiveness of IFN α-2a as an antineoplastic, immunomodulator and antiviral agent has been established.

In another embodiment, polypeptides of the present invention comprising IFN α-2b as well as pharmaceutical compositions comprising the same are indicated for HCL, AIDS-related Kaposi's sarcoma and CHC. It is also indicated for condylomata acuminata (CA), chronic hepatitis B, malignant melanoma and follicular non-Hodgkin's lymphoma. IFN α-2b dosage varies depending on its indication of usage.

In another embodiment, polypeptides of the present invention comprising IFN β are administered in a dose of 1-90 micrograms in 0.1-5 ml solution. In another embodiment, polypeptides of the present invention comprising IFN β are administered in a dose of 1-50 micrograms in 0.1-5 ml solution. In another embodiment, polypeptides of the present invention comprising IFN β are administered in a dose of 1-25 micrograms in 0.1-5 ml solution. In another embodiment, polypeptides of the present invention comprising IFN β are administered in a dose of 50-90 micrograms in 0.1-5 ml solution. In another embodiment, polypeptides of the present invention comprising IFN β are administered in a dose of 10-50 micrograms in 0.1-5 ml solution. In another embodiment, polypeptides of the present invention comprising IFN β are administered in a dose of 1-90 micrograms in 0.1-5 ml solution by intramuscular (IM) injection once a week. In another embodiment, polypeptides of the present invention comprising IFN β are administered in a dose of 1-90 micrograms in 0.1-5 ml solution by intramuscular (IM) injection twice a week. In another embodiment, polypeptides of the present invention comprising IFN β are administered in a dose of 1-90 micrograms in 0.1-5 ml solution by intramuscular (IM) injection three times a week. In another embodiment, polypeptides of the present invention comprising IFN β are administered in a dose of 1-90 micrograms in 0.1-5 ml solution by intramuscular (IM) injection once every two weeks. In another embodiment, polypeptides of the present invention comprising IFN β are administered in a dose of 1-90 micrograms in 0.1-5 ml solution by intramuscular (IM) injection once every 17 days. In another embodiment, polypeptides of the present invention comprising IFN β are administered in a dose of 1-90 micrograms in 0.1-5 ml solution by intramuscular (IM) injection once every 19 days weeks. Assaf-Does this paragraph include IV and SC administration.

In another embodiment, polypeptides of the present invention comprise recombinant IFN. In another embodiment, polypeptides of the present invention comprise recombinant IFN-β. In another embodiment, polypeptides of the present invention comprise recombinant IFN-α. In another embodiment, various recombinant IFN are known to one of skill in the art.

In another embodiment, protein drugs of molecular weight lower than 50,000 daltons, such as interferons, are in general short-lived species in vivo, having short circulatory half-lives of several hours. In another embodiment, the subcutaneous route of administration in general provides slower release into the circulation. In another embodiment, the CTP modified polypeptide of the invention prolongs the half-live of protein drugs of molecular weight lower than 50,000 daltons, such as interferons. In another embodiment, the CTP modified polypeptide of the invention enable interferons to exert their beneficial effects for a longer period of time.

In another embodiment, the immunogenicity of a CTP modified polypeptide comprising IFN is equal to an isolated IFN protein. In another embodiment, the immunogenicity of a CTP modified polypeptide comprising IFN is comparable to an isolated IFN protein. In another embodiment, the CTP modified polypeptide comprising IFN is as active as an isolated IFN protein. In another embodiment, the CTP modified polypeptide comprising IFN is more active than an isolated IFN protein. In another embodiment, the CTP modified polypeptide comprising IFN maximize the IFN protection against degradation while minimizing reductions in bioactivity.

In another embodiment, the polypeptides of the present invention can be provided to the individual per se. In one embodiment, the polypeptides of the present invention can be provided to the individual as part of a pharmaceutical composition where it is mixed with a pharmaceutically acceptable carrier.

In another embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In another embodiment, "active ingredient" refers to the polypeptide sequence of interest, which is accountable for the biological effect.

In another embodiment, any of the compositions of this invention will comprise at least two CTP sequences bound to a protein of interest, in any form. In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In another embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered compound. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In another embodiment, "excipient" refers to an inert substance added to a pharmaceutical composition to further facilitate administration of an active ingredient. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In another embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In another embodiment, the preparation is administered in a local rather than systemic manner, for example, via injection of the preparation directly into a specific region of a patient's body.

Various embodiments of dosage ranges are contemplated by this invention. The dosage of the polypeptide of the present invention, in one embodiment, is in the range of 0.005-10 mg/day. In another embodiment, the dosage is in the range of 0.005-5 mg/day. In another embodiment, the dosage is in the range of 0.01-10 mg/day. In another embodiment, the dosage is in the range of 0.1-10 mg/day. In another embodiment, the dosage is in the range of 0.01-5 mg/day. In another embodiment, the dosage is in the range of 0.001-0.01 mg/day. In another embodiment, the dosage is in the range of 0.001-0.1 mg/day. In another embodiment, the dosage is in the range of 0.1-0.5 mg/day. In another embodiment, the dosage is in the range of 0.5-1 mg/day. In another embodiment, the dosage is in the range of 0.2-1 mg/day. In another embodiment, the dosage is in the range of 0.8-3 mg/day. In another embodiment, the dosage is in the range of 1-5 mg/day. In another embodiment, the dosage is in a range of 5-10 mg/day. In another embodiment, the dosage is in the range of 8-15 mg/day. In another embodiment, the dosage is in a range of 10-20 mg/day. In another embodiment, the dosage is in the range of 20-40 mg/day. In another embodiment, the dosage is in the range of 40-60 mg/day. In another embodiment, the dosage is in a range of 50-100 mg/day. In another embodiment, the dosage is in a range of 1-20 mg/day. In another embodiment, the dosage is in the range of 0.1-50 mg/day. In another embodiment, the dosage is in the range of 0.05-50 mg/day.

In one embodiment, the dosage is 0.01 mg/day. In another embodiment, the dosage is 0.1 mg/day. In another embodiment, the dosage is 1 mg/day. In another embodiment, the dosage is 0.5 mg/day. In another embodiment, the dosage is 0.05 mg/day. In another embodiment, the dosage is 2 mg/day. In another embodiment, the dosage is 10 mg/day. In another embodiment, the dosage is 20 mg/day. In another embodiment, the dosage is 5 mg/day.

In another embodiment, the dosage is 1-90 micrograms mg/day. In another embodiment, the dosage is 1-90 micrograms mg/2 days. In another embodiment, the dosage is 1-90 micrograms mg/3 days. In another embodiment, the dosage is 1-90 micrograms mg/4 days. In another embodiment, the dosage is 1-90 micrograms mg/5 days. In another embodiment, the dosage is 1-90 micrograms mg/6 days. In another embodiment, the dosage is 1-90 micrograms mg/week. In another embodiment, the dosage is 1-90 micrograms mg/9 days. In another embodiment, the dosage is 1-90 micrograms mg/11 days. In another embodiment, the dosage is 1-90 micrograms mg/14 days.

In another embodiment, the dosage is 10-50 micrograms mg/day. In another embodiment, the dosage is 10-50 micrograms mg/2 days. In another embodiment, the dosage is 10-50 micrograms mg/3 days. In another embodiment, the dosage is 10-50 micrograms mg/4 days. In another embodiment, the dosage is 10-50 micrograms mg/5 days. In another embodiment, the dosage is 10-50 micrograms mg/6 days. In another embodiment, the dosage is 10-50 micrograms mg/week. In another embodiment, the dosage is 10-50 micrograms mg/9 days. In another embodiment, the dosage is 10-50 micrograms mg/1 days. In another embodiment, the dosage is 10-50 micrograms mg/14 days.

Oral administration, in one embodiment, comprises a unit dosage form comprising tablets, capsules, lozenges, chewable tablets, suspensions, emulsions and the like. Such unit dosage forms comprise a safe and effective amount of the desired compound polypeptide of the invention. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.001% to about 0.933% of the desired compound or compounds, or in another embodiment, from about 0.01% to about 1%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.001% to about 10.0% w/v of a subject compound, more preferably from about 00.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the active ingredient is in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the active material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved.

In one embodiment, the amount of a composition to be administered will, of course, be dependent on the subject being treated, the severity of the affliction, the manner of administration, the judgment of the prescribing physician, etc.

In one embodiment, compositions including the preparation of the present invention formulated in a compatible pharmaceutical carrier are also be prepared, placed in an appropriate container, and labeled for treatment of an indicated condition.

In another embodiment, a polypeptide as described herein is administered via systemic administration. In another embodiment, a polypeptide as described herein is administered by intravenous, intramuscular or subcutaneous injection. In another embodiment, a polypeptide as described herein is lyophilized (i.e., freeze-dried) preparation in combination with complex organic excipients and stabilizers such as nonionic surface active agents (i.e., surfactants), various sugars, organic polyols and/or human serum albumin. In another embodiment, a pharmaceutical composition comprises a lyophilized polypeptide as described in sterile water for injection. In another embodiment, a pharmaceutical composition comprises a lyophilized polypeptide as described in sterile PBS for injection. In another embodiment, a pharmaceutical composition comprises a lyophilized polypeptide as described in sterile 0.9% NaCl for injection.

In another embodiment, the pharmaceutical composition comprises a polypeptide as described herein and complex carriers such as human serum albumin, polyols, sugars, and anionic surface active stabilizing agents. See, for example, WO 89/10756 (Hara et al.—containing polyol and p-hydroxybenzoate). In another embodiment, the pharmaceutical composition comprises a polypeptide as described herein and lactobionic acid and an acetate/glycine buffer. In another embodiment, the pharmaceutical composition comprises a polypeptide as described herein and amino acids, such as arginine or glutamate that increase the solubility of interferon compositions in water. In another embodiment, the pharmaceutical composition comprises a lyophilized polypeptide as described herein and glycine or human serum albumin (HSA), a buffer (e.g. acetate) and an isotonic agent (e.g NaCl). In another embodiment, the pharmaceutical composition comprises a lyophilized polypeptide as described herein and phosphate buffer, glycine and HSA.

In another embodiment, the pharmaceutical composition comprising a polypeptide as described herein is stabilized when placed in buffered solutions having a pH between about 4 and 7.2. In another embodiment, the pharmaceutical composition comprising a polypeptide as described herein is stabilized with an amino acid as a stabilizing agent and in some cases a salt (if the amino acid does not contain a charged side chain).

In another embodiment, the pharmaceutical composition comprising a polypeptide as described herein is a liquid composition comprising a stabilizing agent at between about 0.3% and 5% by weight which is an amino acid.

In another embodiment, the pharmaceutical composition comprising a polypeptide as described herein provides dosing accuracy and product safety. In another embodiment, the pharmaceutical composition comprising a polypeptide as described herein provides a biologically active, stable liquid formulation for use in injectable applications. In another embodiment, the pharmaceutical composition comprises a non-lyophilized polypeptide as described herein.

In another embodiment, the pharmaceutical composition comprising a polypeptide as described herein provides a liquid formulation permitting storage for a long period of time in a liquid state facilitating storage and shipping prior to administration.

In another embodiment, the pharmaceutical composition comprising a polypeptide as described herein comprises solid lipids as matrix material. In another embodiment, the injectable pharmaceutical composition comprising a polypeptide as described herein comprises solid lipids as matrix material. In another embodiment, the production of lipid microparticles by spray congealing was described by Speiser (Speiser and al., Pharm. Res. 8 (1991) 47-54) followed by lipid nanopellets for peroral administration (Speiser EP 0167825 (1990)). In another embodiment, lipids, which are used, are well tolerated by the body (e.g. glycerides composed of fatty acids which are present in the emulsions for parenteral nutrition).

In another embodiment, the pharmaceutical composition comprising a polypeptide as described herein is in the form of liposomes (J. E. Diederichs and al., Pharm./nd. 56 (1994) 267-275).

In another embodiment, the pharmaceutical composition comprising a polypeptide as described herein comprises polymeric microparticles. In another embodiment, the injectable pharmaceutical composition comprising a polypeptide as described herein comprises polymeric microparticles. In another embodiment, the pharmaceutical composition comprising a polypeptide as described herein comprises nanoparticles. In another embodiment, the pharmaceutical composition comprising a polypeptide as described herein comprises liposomes. In another embodiment, the pharmaceutical composition comprising a polypeptide as described herein comprises lipid emulsion In another embodiment, the pharmaceutical composition comprising a polypeptide as described herein comprises microspheres. In another embodiment, the pharmaceutical composition comprising a polypeptide as described herein comprises lipid nanoparticles. In another embodiment, the pharmaceutical composition comprising a polypeptide as described herein comprises lipid nanoparticles comprising amphiphilic lipids. In another embodiment, the pharmaceutical composition comprising a polypeptide as described herein comprises lipid nanoparticles comprising a drug, a lipid matrix and a surfactant. In another embodiment, the lipid matrix has a monoglyceride content which is at least 50% w/w.

In one embodiment, compositions of the present invention are presented in a pack or dispenser device, such as an FDA approved kit, which contain one or more unit dosage forms containing the active ingredient. In one embodiment, the pack, for example, comprise metal or plastic foil, such as a blister pack. In one embodiment, the pack or dispenser device is accompanied by instructions for administration. In one embodiment, the pack or dispenser is accommodated by a notice associated with the container in a form prescribed by a governmental agency regulating the manufacture, use or sale of pharmaceuticals, which notice is reflective of approval by the agency of the form of the compositions or human or veterinary administration. Such notice, in one embodiment, is labeling approved by the U.S. Food and Drug Administration for prescription drugs or of an approved product insert.

In one embodiment, it will be appreciated that the polypeptides of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference. Other general references are provided throughout this document.

Example 1

Construction of h IFNβ-CTP Variants

Construction of hIFNβ-CTP variants: A cassette gene containing the C-Terminal peptide (CTP) of the beta subunit of hCG was fused to the coding sequence of human IFN beta 1a (SEQ ID NO: 2) at different locations. Seven IFNβ-CTP variants were constructed as illustrated in FIGS. 1A-G. The proIFNβ signal peptide was used for the construction of the secreted IFNβ-CTP variants. XbaI-NotI fragments containing IFNβ sequences were ligated into the pCI-dhfr expression vector of the present invention.

Table 2 hereinbelow summarizes the primer sequences used for constructing the CTP-containing polypeptides of the present invention.

TABLE 2

| Primer number | SEQ ID NO | Sequence | Restriction Site (underlined in sequence) |
|---|---|---|---|
| 40 | 20 | 5' GAAT<u>TCTAGA</u>GGACATGACCAAC 3' | XbaI |
| 41$^R$ | 21 | 5' <u>GCGGCCGC</u>GGACTCATCAGTTCCTCA GGTAGCCG 3' | NotI |

IFNβ-1 901-1-p107-2 (IFNβ-1-SEQ ID NO: 6): The IFNβ-ctp clone was synthesized by GeneArt (Geneart No. 0609229).

Then the XbaI-NotI fragment containing IFNβ-ctp sequence was ligated into pCI-dhfr expression vector. The amino acid sequence of this clone is presented in SEQ ID NO: 5.

IFNβ-2 901-2-p113-3 (IFNβ-2-SEQ ID NO: 8): The XbaI/ApaI fragment (IFN-ctp) of pCI-dhfr-701-2-p24-2 (IFN-ctpx2) was replaced by the XbaI/ApaI fragment (IFNβ-ctp) of 901-1-p107-2 to create a IFNβctpx2 clone. The amino acid sequence of this clone is presented in SEQ ID NO: 7.

IFNβ-4 901-4-p108-16 (IFNβ-4-SEQ ID NO: 12): The ctp-IFNβ-ctp-IFNβclone was synthesized by GeneArt (Geneart No. 0609227).

Then the XbaI-NotI fragment containing sequence ctp-IFNβ-ctp-IFNβ was ligated into pCI-dhfr expression vector. The amino acid sequence of this clone is presented in SEQ ID NO: 11.

IFNβ-6 901-6-p109-3 (IFNβ-6 SEQ ID NO; 16): The ctp-IFNβ-ctp clone was synthesized by GeneArt (Geneart No. 0609228).

Then the XbaI-NotI fragment containing sequence ctp-IFNβ-ctp was ligated into pCI-dhfr expression vector. The amino acid sequence of this clone is presented in SEQ ID NO: 15.

IFNβ-5-p103-10 (IFNβ-5 SEQ ID NO; 14-(ctp-IFNβ): Primers were ordered from Sigma-Genosys. A PCR reaction was performed using primer 40 (SEQ ID NO: 20) and primer 41$^R$ (SEQ ID NO:21) and plasmid DNA of the synthesized ctp-IFNβ-ctp (Geneart No. 0609228) as a template; as a result of the PCR amplification, a 677 bp product was formed. The PCR fragment was digested with XbaI-NotI and the fragment containing ctp-IFNβ sequence was ligated into our eukaryotic expression vector pCI-dhfr to yield the 901-5-p103-10 clone. The amino acid sequence of this clone is presented in SEQ ID NO: 13.

IFNβ-3 901-3-p114-5 (IFNβ-3 SEQ ID NO: 10-(ctp-IFN-CTP(x2)): The XbaI/ApaI fragment (IFN-ctp) of pCI-dhfr-701-2-p24-2 (IFN-ctpx2) was replaced by the XbaI/ApaI fragment (ctp-IFNβ-ctp) of 901-6-p109-3 to create a ctp-IFNβctpx2 clone. The amino acid sequence of this clone is presented in SEQ ID NO: 9.

IFNβ-901-0-p102-1 (IFNβ-0 SEQ ID NO; 2-(IFNβ): Primers were ordered from Sigma-Genosys. A PCR reaction was performed using primer 40 (SEQ ID NO:20) and primer 41$^R$ (SEQ ID NO:21) and plasmid DNA of the synthesized IFNβ-ctp (Geneart No. 0609229) as a template; as a result of the PCR amplification, a 599 bp product was formed. The PCR fragment was digested with XbaI-NotI and the fragment containing IFNβ sequence was ligated into our eukaryotic expression vector pCI-dhfr to yield the 901-0-p102-1 clone. The amino acid sequence of this clone is presented in SEQ ID NO: 1.

Example 2

Expression and Isolation of IFN-CTP Polypeptides

Materials and Methods

DNA transfection and clone selection: DG44 cells were transfected with pCI-DHFR expression vectors containing IFNβ-CTP variants using FuGENE6 Reagent (FuGENE Transfection Reagent—Roche Cat. 11 1815 091 001). 48 hr following transfection, cells were diluted and seeded at 50-200 cells per well in a selective medium (CD DG44 Medium w/o HT (Gibco: Scotland part: #07990111A) Sku num.:ME060027 supplemented with 8 mM L-Glutamine Biological Industries: Cat: 03-020-1A) and 18 mL/L of 10% Pluronic F-68 solution (Gibco: Cat: 240040-032). Selected clones were screened for highest protein production using commercial ELISA. 3-5 producing clones per each variant were frozen for a backup cell bank. A selected clone for each variant was adapted to growth in larger scale cultures up to IL flasks on an orbital shaker platform. Supernatants were collected and analyzed by ELISA, SDS-PAGE and western blot. Following the withdrawal of aliquots, the protein-containing supernatants were kept frozen until further use.

Cell culture: DG44 cells were maintained in DG44 medium with HT (cat#12610-010, Gibco) supplemented with 8 mM L-Glutamine (Biological Industries: Cat: 03-020-1A) and 18 mL/L of 10% Pluronic F-68 solution (Gibco: Cat: 240040-032), at 37° C. in humidified 8% $CO_2$ incubator. Transfected clones were maintained in DG44 basal medium without HT supplement, hypoxanthine and thymidine, with pluronic acid and L-glutamine.

Sample preparation: Supernatants were collected, filtrated and analyzed by ELISA to determine protein concentration. SDS-PAGE and western blot were used to determine purity and identity. Following ELISA, sample concentrations were defined and the solution was dialyzed against PBS. Following the withdrawal of aliquots, the protein-contained supernatants were kept frozen at −20° C. until further use.

Western Blotting Samples were electrophoresed on non-denaturing 15% SDS-polyacrylamide gels. Gels were allowed to equilibrate for 10 min in 25 mM Tris and 192 mM glycine in 20% (vol/vol) methanol. Proteins were transferred to a 0.2 μm pore size nitrocellulose membrane (Sigma, Saint Louis, Mo.) at 250 mA for 3 h, using a Mini Trans-Blot electrophoresis cell (Biorad Laboratories, Richmond, Calif.). The nitrocellulose membrane was incubated in 5% non-fat dry milk for 2 h at room temperature. The membrane was incubated with IFN anti-serum (1:1000 titer) overnight at 4° C. followed by three consecutive washes in PBS containing 0.1% Tween (10 min/wash). The membrane was incubated with secondary antibody conjugated to Horse Radish Peroxidase (HRP) (Zymed, San Francisco, Calif.) for 2 h at room temperature, followed by three washes. Finally, the nitrocellulose paper was reacted with enhanced chemiluminescent substrate (ECL) (Pierce, Rockford, Ill.) for 5 min, dried with a Whatman sheet, and exposed to X-ray film.

FIG. 1 indicates that MOD-901X-variants are recognized by anti IFN-β1a antibodies. The SDS PAGE gel was stained using coomassie blue (a) or (B). blotted and stained using monoclonal anti-IFN-β1a antibodies Example 3

The IFN-CTP Polypeptides are Bioactive

To determine the bioactivity of MOD-901X variants through its recognition and binding to the IFN receptor. Daudi cell line (human Burkitt lymphoma) ATCC catalog No, CCL-213 TM (one of the most sensitive cell lines to the anti-proliferative effect of IFN-β1a) were used. Daudi cells, grown in suspension were treated with different concentrations of IFN-β1a (50-1000 pg/ml final concentration) and incubated for 72 hours. The number of viable cells was measured using CellTiter 96® AQueous One Solution Cell Proliferation Assay kit (Promega G3580) according to manufacturer procedures. The assay's standard curve was prepared using recombinant human IFN-β1a (PtoSpec-Tany Techno-Gene).

IFN-β1a is a cytokine that exhibit antiviral activity against a variety of viruses. The potency of IFN-β1a as an antiviral agent can be determined by a viral cytophatic effect (CPE) bioassay that measures the ability of the protein to protect human lung carcinoma A549 cells (grown at 37° C., 5% $CO_2$) challenged with encephalomyocarditis (ECM) virus. A549 cells were plated into 96 well microtiter plate. Serial dilutions of IFN-β1a standards and test samples were added and 24 h later the cells were challenged with ECP virus. Viable cells were quantified two days later.

The potency (titer) of an IFN-β1 a test sample is determined as the reciprocal of the dilution represented in the well in which 50% of the cell monolayer is protected from the CPE virus. The actual potency is calculated by comparing the sample's protective effect with the same effect of a reference standard calibrated in International Units, provided by the National Institute of Allergy and Infectious Diseases (NIH). The results are shown in Table 3.

TABLE 3

| | Specific Activity IU/mg × 10^8 | | |
|---|---|---|---|
| | Anti-viral | Anti-proliferation | IC50 pg/ml |
| Intl. Standard | | 2.00 | 318 |
| IFNb-0 | 3.90 | 2.53 | 251 |
| IFNb-1 | 4.00 | 2.41 | 264 |
| IFNb-2 | 4.00 | 1.90 | 334 |
| IFNb-3 | 4.00 | 2.77 | 230 |
| IFNb-5 | 4.00 | 6.24 | 102 |
| IFNb-6 | 3.70 | 1.97 | 323 |

*concentration was determined by Elisa assay

Conclusion: The activity of MOD-901X variants as measured by its antiviral effects were at normal range of the Intl' standard and similar to rhIFN. Same effect was observed in anti-proliferation assay except for MOD-9015 which was 3 times more potent than the other variants. IFNb-0 is (SEQ ID NO: 1). IFNb-1 is (SEQ ID NO: 5, MOD-9011). IFNb-2 is (SEQ ID NO: 7, MOD-9012). IFNb-3 is (SEQ ID NO: 9, MOD-9013). IFNb-4 is (SEQ ID NO: 11, MOD-9014). IFNb-5 is (SEQ ID NO: 13, MOD-9015). IFNb-6 is (SEQ ID NO: 15, MOD-9016).

Example 4

Comparative Pharmacokinetics (Mod-901X Variants, Avonex and Rebif)

In order to determine the pharmacokinetics of MOD-901x and compare it to that of commercial IFN-β1a (Rebif, Avonex) data statistical analysis was performed. The analysis included analysis of serum samples that was performed in order to determine specific concentration levels for each sample. Concentration and time-point data were processed using WinNonLin nocomparmental analysis. The following parameters were determined: AUC, CL, Ke, t1/2, Cmax, Tmax, and Vdz.

The experimental design is provided in table 4.

TABLE 4

| No. | Drug | N | Route | Species Gender | Equimolar Dose (µg/Kg) | Dose Vol.(ml) | Time-points ± (hours post-dose) |
|---|---|---|---|---|---|---|---|
| 1 | Avonex | 3 | IV/SC | SD rat/Male | 38/66 | 0.3/0.5 | 0 (Pre-dose) 0.5, 4, 8, 24, 48, 96. |
| 2 | Rebif | 3 | IV/SC | SD rat/Male | 38/66 | 0.3/0.5 | 0.5, 4, 8, 24, 48, 96. |
| 3 | MOD-9011 | 3 | IV/SC | SD rat/Male | 38/66 | 0.3/0.5 | 0.5, 4, 8, 24, 48, 96. |
| 4 | MOD-9012 | 3 | IV/SC | SD rat/Male | 38/66 | 0.3/0.5 | 0.5, 4, 8, 24, 48, 96. |
| 5 | MOD-9013 | 3 | IV/SC | SD rat/Male | 38/66 | 0.3/0.5 | 0.5, 4, 8, 24, 48, 96. |
| 6 | MOD-9015 | 3 | IV/SC | SD rat/Male | 38/66 | 0.3/0.5 | 0.5, 4, 8, 24, 48, 96. |
| 7 | MOD-9016 | 3 | IV/SC | SD rat/Male | 38/66 | 0.3/0.5 | 0.5, 4, 8, 24, 48, 96. |

3 rats per time point.

Figure 2:
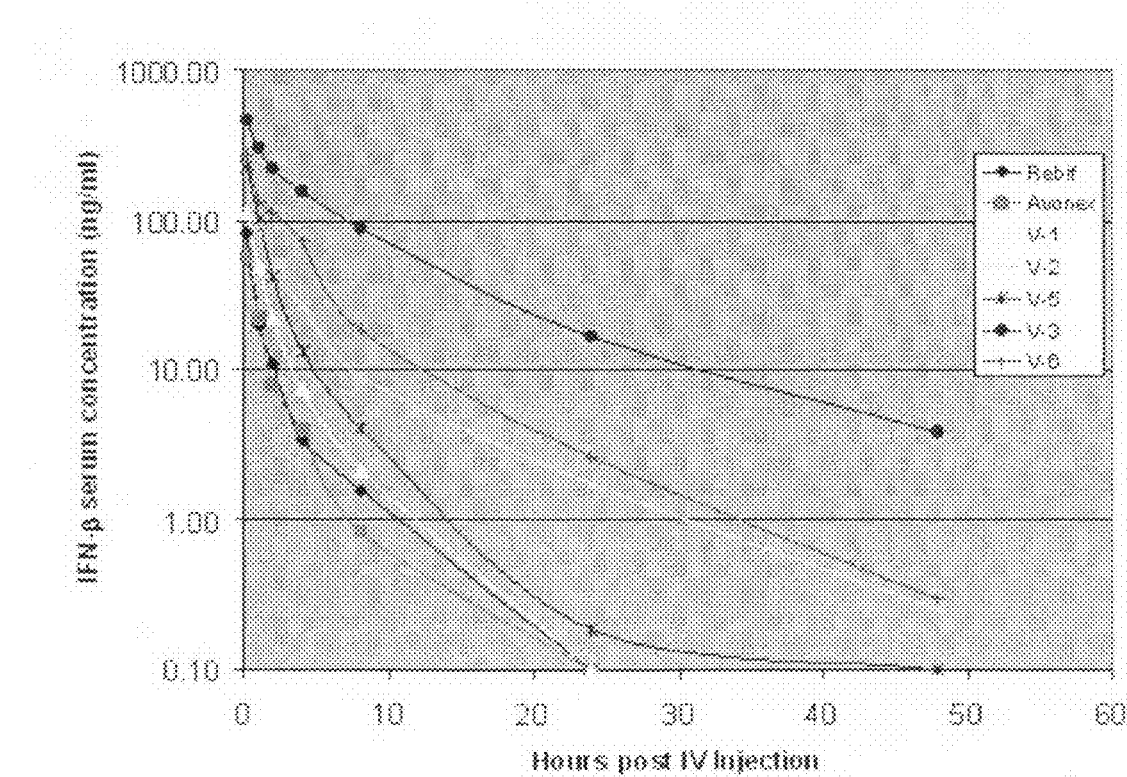
FIG. 2 Mean plasma IFN-β1a or MOD-901x variants concentrations (ng/ml) following single-dose IV administration of IFN-β1a or MOD-901x variants in SD rats (n=3 per dose/route/timepoint). IFN-β1a serum concentrations were determined using commercial ELISA kit.

FIG. 2 show the change in serum concentration of IFN-β1a or MOD-901x concentrations (ng/ml) following single-dose IV administration of IFN-β1a or MOD-901x in SD rats.

Table 5 show the mean pharmacokinetic parameters following single-dose IV or Sub-Cutaneous (SC) administration of IFN-β1a and MOD-901x in Spargue-Dawley rats.

TABLE 5

| | | PK Statistics | | | | | | |
|---|---|---|---|---|---|---|---|---|
| Parameters | Units | Avonex | Rebif | MOD-9011 | IV MOD-9012 | MOD-9015 | MOD-9013 | MOD-9016 |
| Dose | µq | 5 | 5 | 5 | 5 | 5 | 5 | 5 |
| AUClast | hr*ng/mL | 83.9 | 106.4 | 185.3 | 417 | 369.4 | 2562.9 | 879.6 |
| Cmax | ng/ml | | | | | | | |
| Tmax | hr | | | | | | | |
| MRT | hr | 1.5 | 1.3 | 2.1 | 11.3 | 2 | 12.1 | 9.6 |
| T½ α | hr | 1.02 | 0.9 | 1.43 | 2.17 | 1.4 | 2.53 | 2.22 |
| T½ β | hr | | | | 7.82 | | 8.36 | 6.66 |

Parameters was generated for individual rats and the mean data are presented here.

In conclusion: IFN-β1a with 3 CTP units has 8 times longer half-life than that of Rebif or Avonex when injected IV.

Figure 4:
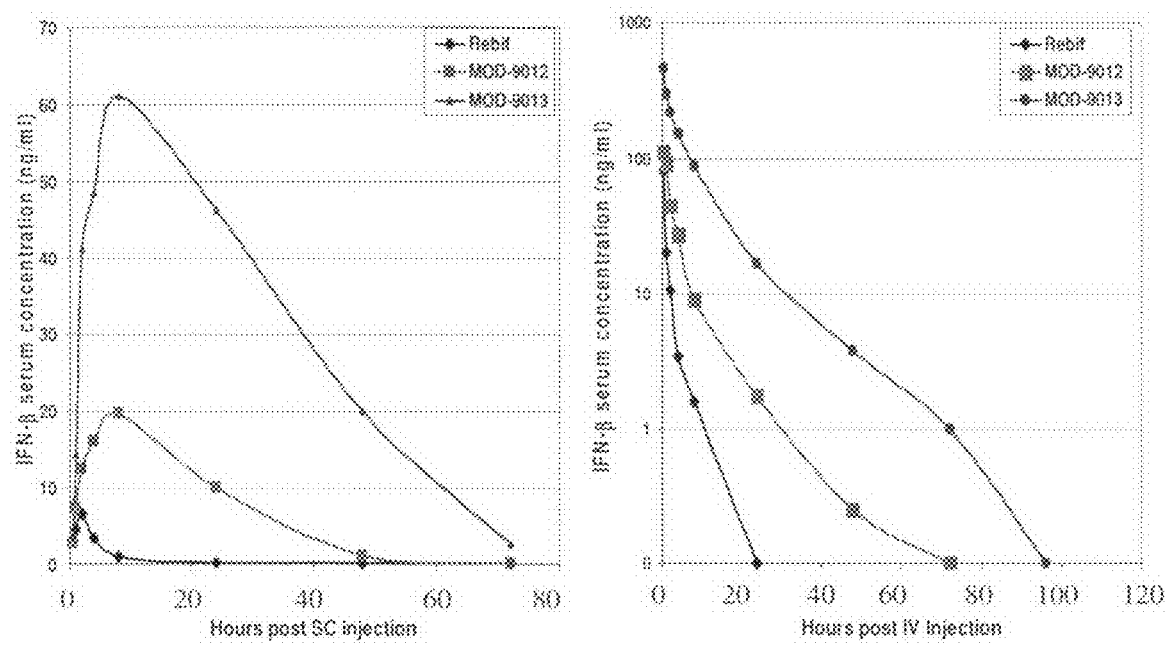
FIG. 4 are graphs showing the mean plasma concentrations (ng/ml) of Rebif, MOD-9012, and MOD-9013 following single-dose IV or SC administration of IFN-β1a or MOD-9012, and MOD-9013 in SD rats (n=3 per dose/route/timepoint). IFN-β1a serum concentrations were determined using commercial ELISA kit.

FIG. 4 shows the mean plasma of Rebif, MOD-9012, and MOD-9013 concentrations (ng/ml) following single-dose IV or SC administration of IFN-β1a, MOD-9012 or MOD-9013 in SD rats (n=3 per dose/route/timepoint). IFN-β1a serum concentrations were determined using commercial ELISA kit.

Table 6 displays the mean pharmacokinetic parameters following single-dose IV or SC administration of Rebif, MOD-9012, and MOD-9013 in Spargue-Dawley rats.

TABLE 6

| | | SC | | | | IV | | |
|---|---|---|---|---|---|---|---|---|
| Parameters | Units | Rebif | MOD-9012 | MOD-9013 | Parameters | Rebif | MOD-9012 | MOD-9013 |
| Dose | μq | 10 | 10 | 10 | Dose | 5 | 5 | 5 |
| AUClast | hr*ng/mL | 34.8 | 498.5 | 2299.5 | AUClast | 106.4 | 417 | 2562.9 |
| Cmax | ng/ml | 6.6 | 19.7 | 61.1 | Cmax | | | |
| Tmax | hr | 2 | 8 | 8 | Tmax | | | |
| MRT | hr | 4.1 | 15.9 | 24.1 | MRT | 1.3 | 11.3 | 12.1 |
| T½ ab | hr | 0.6 | 2.75 | 3.1 | T½ α | 0.9 | 2.17 | 2.53 |
| T½ el | hr | 2.1 | 9.5 | 14.2 | T½ β | | 7.82 | 8.36 |

Parameters were generated for individual rats and the mean data are presented.

In conclusion, IFN-β1a with 3 CTP units (MOD-9013) has 9.2 times longer half-life than that of Rebif when injected IV and 6.7 times longer half-life when injected SC. AUClast of MOD-9013 is 66 times better then Rebif when injected SC and 24 times when injected IV. MRT of MOD-9013 is 5.8 times better when injected SC and 9.3 times when injected Iv.

The MOD-9013 molecule which comprises one CTP attached to the N-terminus of IFN-β1a and two CTP attached to its C-terminus was tested in-vitro for its ability to bind to the human IFN receptor and in-vivo for its pharmacokinetic performance. The conclusions of these studies can be summarized as follows: (1) The in-vitro anti-proliferation activity of MOD-9013 as demonstrated in the daudi cells assay was similar to the international standard and to that of MOD-9010 (rIFN-β1a expressed by Modigene). (2) The anti-viral protective activity of MOD-9013 shown in Daudi cells was same as the international standard and as of that of MOD-9010 (rIFN-β1a expressed by Modigene). (3) In terms of its pharmacokinetic features MOD-9013 was compared in SD rats to Rebif and Avonex. Following a single IV/SC injection of 38/66 μg/kg, Clearance of MOD-9013 from SD rats blood was significantly slower than that for Rebif and Avonex. The corresponding calculated half life times and AUCs were: For IV administration:

| For IV administration: | |
|---|---|
| Rebif | T½ 1 h, AUC106 hr*ng/mL |
| MOD-9013 | T½ 8.4 h, AUC2563 hr*ng/mL |
| For SC administration: | |
| Rebif | T½ 2.1 h, AUC34.8 hr*ng/mL |
| MOD-9013 | T½ 14.2 h, AUC2299.5 hr*ng/mL |

The superior performance of MOD-9013 to stimulate anti-viral and anti-proliferation activity and to retain long lasting stimulation results from three main reasons: i) Addition of up to 24 sialic acid residues; ii) Stabilizing effect on the IFN-β1a molecule by fusing the CTP cassettes to both N and C termini; and iii) Increase in molecular weight of the whole molecule from ~31,242-48,000 Daltons.

As shown hereinabove, different levels of potency were exerted by IFN-CTP polypeptides, indicating differences in receptor binding. IFN-CTP polypeptides differ by the number of CTP cassettes and the location to which they are fused. MOD-9011 and MOD-9012 contain 1 CTP sequence or 2 CTP sequences at the C-terminal of IFN protein, while MOD-9013 contains 1 CTP at N-terminal and 2 CTP sequences at C-terminal. MOD-9014 is a dimer of two IFN molecules linked by CTP sequence. MOD-9013 demonstrated unexpected potency level.

What is claimed is:

1. A CTP-modified interferon protein consisting of an interferon (IFN) protein, one chorionic gonadotrophin carboxy terminal peptide (CTP) attached to the amino terminus of said interferon protein and two chorionic gonadotrophin carboxy terminal peptides attached to the carboxy terminus of said interferon protein.

2. The CTP-modified interferon protein of claim 1, wherein the sequence of at least one CTP consists of an amino acid sequence selected from the group consisting of: SEQ ID NO: 17 and SEQ ID NO: 18.

3. The CTP-modified interferon protein of claim 1, wherein said interferon is a type I interferon.

4. The CTP-modified interferon protein of claim 3, wherein said type I interferon is IFN-α or IFN-β.

5. The CTP-modified interferon protein of claim 1, wherein said interferon is IFN-γ.

6. The CTP-modified interferon protein of claim 1, wherein at least one CTP is glycosylated.

7. The CTP-modified interferon protein of claim 1, wherein at least one CTP is truncated.

8. The CTP-modified interferon protein of claim 1, wherein the sequence of said polypeptide consists of the amino acid sequence of MOD 9013 as set forth in SEQ ID NO: 9.

9. The CTP-modified interferon protein of claim 1, wherein at least one CTP is attached to said interferon protein via a linker.

10. The CTP-modified interferon protein of claim 9, wherein said linker is a peptide bond.

11. The CTP-modified interferon protein of claim 1, wherein said interferon protein includes a signal peptide.

12. The CTP-modified interferon protein of claim 11, wherein the amino acid sequence of said signal peptide is as set forth in SEQ ID NO: 19.

13. A pharmaceutical composition comprising the CTP-modified interferon protein of claim 1 and a pharmaceutically acceptable carrier.

14. A method of reducing the clearance rate of an interferon protein, consisting of the step of attaching one chorionic gonadotrophin carboxy terminal peptide (CTP) to the amino terminus of said interferon protein and two chorionic gonadotrophin carboxy terminal peptides to the carboxy terminus of said interferon protein, thereby reducing the clearance rate of an interferon protein.

15. The method of claim 14, wherein the sequence of at least one chorionic gonadotrophin carboxy terminal peptide consists of an amino acid sequence selected from the group consisting of: SEQ ID NO: 17 and SEQ ID NO: 18.

16. The method of claim 14, wherein the sequence of said CTP-modified interferon protein consists of the amino acid sequence of MOD 9013 as set forth in SEQ ID NO: 9.

17. The method of claim 14, wherein said interferon protein includes a signal peptide.

18. The method of claim 17, wherein the amino acid sequence of said signal peptide is as set forth in SEQ ID NO: 19.

19. The method of claim 14, wherein said interferon is a type I interferon.

20. The method of claim 14, wherein at least one CTP is truncated.

21. A method of reducing the dosing frequency of an interferon protein therapy in a subject, consisting of the step of attaching one chorionic gonadotrophin carboxy terminal peptide (CTP) to the amino terminus of said interferon protein, and two chorionic gonadotrophin carboxy terminal peptides (CTPs) to the carboxy terminus of said interferon protein, thereby reducing the dosing frequency of an interferon protein therapy in a subject.

22. The method of claim 21, wherein the sequence of at least one CTP consists of an amino acid sequence selected from the group consisting of: SEQ ID NO: 17 and SEQ ID NO: 18.

23. The method of claim 21, wherein said interferon protein includes a signal peptide.

24. The method of claim 23, wherein the amino acid sequence of said signal peptide is as set forth in SEQ ID NO: 19.

25. The method of claim 21, wherein the sequence of said CTP-modified interferon protein consists of the amino acid sequence of MOD 9013 as set forth in SEQ ID NO: 9.

26. The method of claim 21, wherein said interferon is a type I interferon.

27. The method of claim 21, wherein at least one CTP is truncated.

28. A method of improving the area under the curve (AUC) of an interferon protein in a subject, consisting of the step of attaching one chorionic gonadotrophin carboxy terminal peptide (CTP) to the amino terminus of said interferon protein and two chorionic gonadotrophin carboxy terminal peptides (CTPs) to the carboxy terminus of said interferon protein, thereby improving the area under the curve (AUC) of an interferon protein in a subject.

29. The method of claim 28, wherein the sequence of at least one CTP consists of an amino acid sequence selected from the group consisting of: SEQ ID NO: 17 and SEQ ID NO: 18.

30. The method of claim 28, wherein said interferon protein includes a signal peptide.

31. The method of claim 30, wherein the amino acid sequence of said signal peptide is as set forth in SEQ ID NO: 19.

32. The method of claim 28, wherein the sequence of said CTP-modified interferon protein consists of the amino acid sequence of MOD 9013 as set forth in SEQ ID NO: 9.

33. The method of claim 28, wherein said interferon is a type I interferon.

34. The method of claim 28, wherein at least one CTP is truncated.

* * * * *